United States Patent [19]

Snell et al.

[11] Patent Number: 5,309,919

[45] Date of Patent: May 10, 1994

[54] METHOD AND SYSTEM FOR RECORDING, REPORTING, AND DISPLAYING THE DISTRIBUTION OF PACING EVENTS OVER TIME AND FOR USING SAME TO OPTIMIZE PROGRAMING

[75] Inventors: Jeffery D. Snell, Northridge; Harold C. Schloss, Los Angeles; Brian M. Mann, Beverly Hills; John W. Poore, South Pasadena; Roy B. Medlin, West Hills, all of Calif.

[73] Assignee: Siemens Pacesetter, Inc., Sylmar, Calif.

[21] Appl. No.: 846,461

[22] Filed: Mar. 2, 1992

[51] Int. Cl.$^5$ .......................................... A61B 5/0452
[52] U.S. Cl. ...................................... 128/697; 607/26
[58] Field of Search ................... 128/419 PT, 419 PG, 128/697; 607/27, 32

[56] References Cited

U.S. PATENT DOCUMENTS

| | | | |
|---|---|---|---|
| 3,820,025 | 6/1974 | Lahr et al. | 324/182 |
| 4,250,888 | 2/1981 | Grosskopf | 128/702 |
| 4,333,475 | 6/1982 | Moreno et al. | 128/711 |
| 4,513,743 | 4/1985 | van Arragon et al. | 128/419 PG |
| 4,559,947 | 12/1985 | Renger et al. | 128/419 PG |
| 4,596,255 | 6/1986 | Snell et al. | 128/697 |
| 4,633,881 | 1/1987 | Moore et al. | 128/659 |
| 4,667,681 | 5/1987 | Baumberg | 128/689 |
| 4,791,936 | 12/1988 | Snell et al. | 128/697 |
| 4,809,697 | 3/1989 | Causey, III et al. | 128/419 PT |
| 4,940,052 | 7/1990 | Mann et al. | 128/419 PG |
| 5,040,534 | 8/1991 | Mann et al. | 128/419 PG |
| 5,056,527 | 10/1991 | Go et al. | 128/702 |

OTHER PUBLICATIONS

Sanders et al., "Data Storage and Retrieval by Implantable Pacemakers for Diagnostic Purposes," PACE, vol. 7, pp. 1228-1233 (Nov.-Dec. 1984, Part II).
Levine, P. A., "Diagnostic Data: An Aid to the Follow-up and Assessment of the Pacing System," Journal of Electrophysiology, vol. 1, pp. 396-403 (1987).
"Chorus 6003-6033 Implantable Dual-Chamber Pulse Generator DDD MO," Physician's Manual, pp. 40-41 (ELA Medical, Minnetonka, Minn.-1990 or earlier).
Luceri et al., "Improved Patient Surveillance and Data Acquisition with a Third Generation Implantable Cardioverter-Defibrillator," PACE, vol. 14, pp. 1870-1874 (Nov. 1991, Part II).

Primary Examiner—William E. Kamm
Attorney, Agent, or Firm—Bryant R. Gold; Leslie S. Miller

[57] ABSTRACT

A method and system for monitoring the behavior of an implanted pacemaker counts (records) the number of times that a given internal event or state change of the pacemaker occurs, and also determines the rate at which each event or state change thus counted occurs. The event counts and their associated rate are stored (recorded) in appropriate memory circuits housed within the pacemaker device. At an appropriate time, the stored event count and rate data are downloaded to an external programming device. The external programming device processes the event count and rate data, and displays a distribution of the event count data as a function of its rate of occurrence, as well as other statistical information derived therefrom. The displayed information, and its associated statistical information, allows a baseline recording to be made that establishes the implanted pacemaker's behavior for a given patient under known conditions. Such baseline recording of event counts in combination with the associated rate of occurrence of such event counts provides significant insight into the past behavior of the pacemaker as implanted in a particular patient. The past behavior of the pacemaker, in turn, may then be used to predict with a high degree of accuracy the future behavior of the pacemaker.

55 Claims, 12 Drawing Sheets

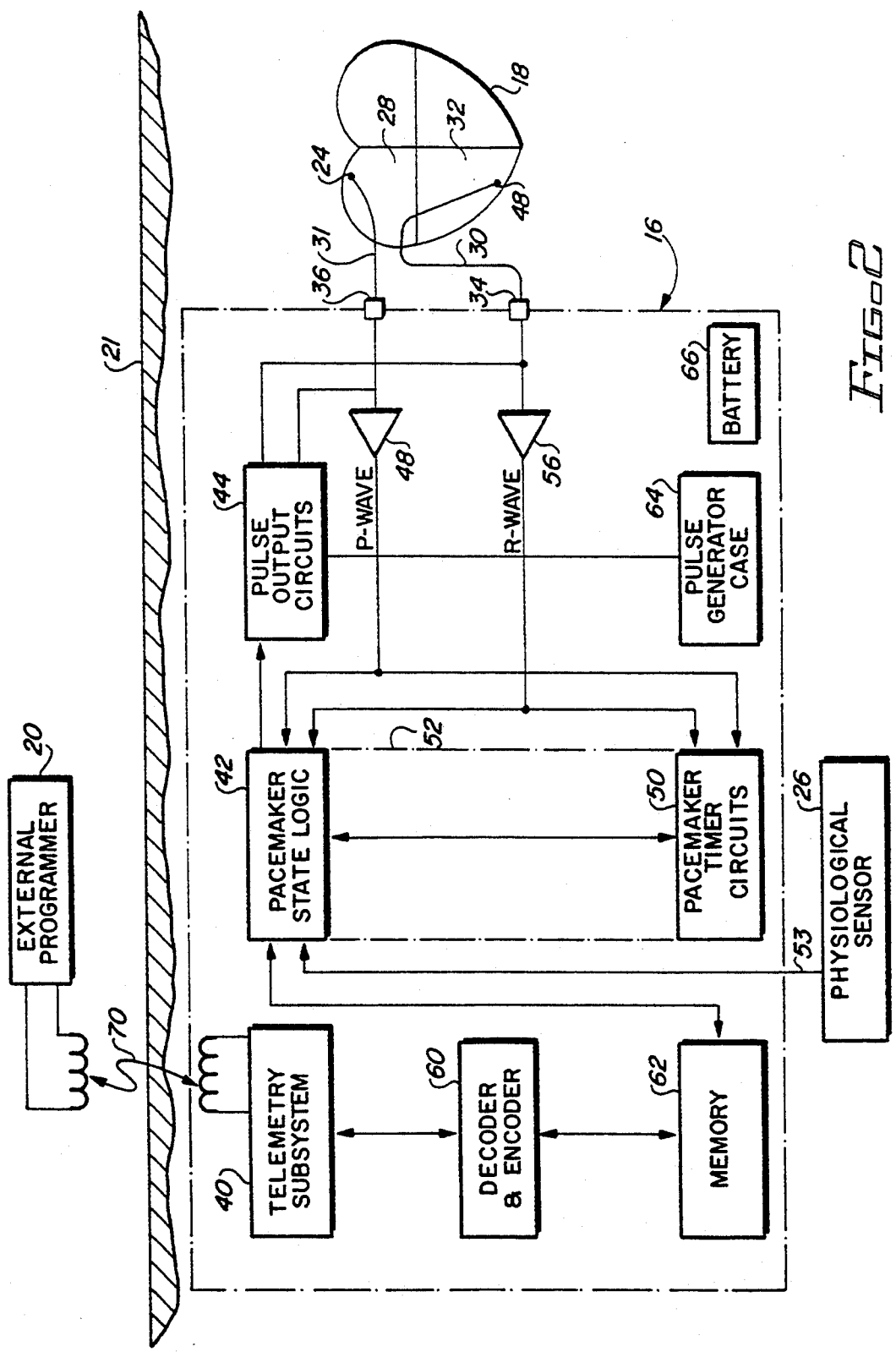

| 210 | 126 | 128 | 120 | 122 | 124 | 130 | 132 |
|---|---|---|---|---|---|---|---|
| RATE ppm | PV | PR | AV | AR | PVC | PV @MTR | PR @MTR |
| 0-60 | 0 | 0 | 3,257,853 | 140,154 | 0 | 0 | 0 |
| 61-67 | 583,335 | 489,684 | 55,493 | 286,402 | 0 | 0 | 0 |
| 68-75 | 1,689,030 | 2,437,840 | 101,970 | 114,093 | 4 | 0 | 0 |
| 76-85 | 1,794,561 | 4,169,512 | 316,511 | 187,534 | 24 | 0 | 0 |
| 86-100 | 525,528 | 2,160,636 | 384,167 | 20,562 | 190 | 0 | 0 |
| 101-119 | 60,985 | 111,049 | 94,454 | 700 | 1,952 | 0 | 0 |
| 120-149 | 19,928 | 664 | 26,521 | 1 | 6,322 | 7 | 0 |
| >149 | 0 | 5 | 0 | 0 | 537 | 0 | 35 |

Synchrony® II

Jan 7 1992 1:00 pm
MODEL: 2022    SERIAL: 14289

PATIENT: _____
PHYSICIAN: _____

EVENT HISTOGRAM

Total Time Sampled 184d 16h 3m 55s
Sampling Rate EVERY EVENT

Mode _____ DDDR
Sensor _____ ON
Rate _____ 70 ppm
Max Track _____ 110 ppm
Maximum Sensor Rate _____ 110 ppm
A-V Delay _____ 175 msec
Rate Resp. A-V Delay _____ ENABLE Note: The above values were obtained
when the histogram was interrogated.

| Rate ppm | PV | PR | Event Counts AV | AR | PVE |
|---|---|---|---|---|---|
| 0-60 | 0 | 0 | 3,257,853 | 140,154 | 0 |
| 61-67 | 583,335 | 489,684 | 55,493 | 286,402 | 0 |
| 68-75 | 1,689,030 | 2,437,840 | 101,970 | 114,093 | 4 |
| 76-85 | 1,794,561 | 4,169,512 | 316,511 | 187,534 | 24 |
| 86-100 | 525,528 | 2,160,636 | 384,167 | 20,562 | 190 |
| 101-119 | 60,985 | 111,849 | 94,454 | 700 | 1,952 |
| 120-149 | 19,935 | 664 | 26,521 | 1 | 6,322 |
| > 149 | 0 | 40 | 0 | 0 | 537 |
| Total: | 4,673,374 | 9,369,425 | 4,236,969 | 749,446 | 9,029 |

Total Event Count: 19,038,243

Percent Paced in Atrium _____ 26%
Percent Paced in Ventricle _____ 47%
Total Time at Max Track Rate _____ 0d 0h 0m 3s

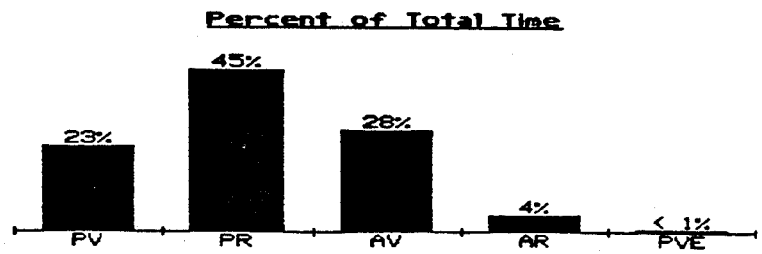

FIG. 19

METHOD AND SYSTEM FOR RECORDING, REPORTING, AND DISPLAYING THE DISTRIBUTION OF PACING EVENTS OVER TIME AND FOR USING SAME TO OPTIMIZE PROGRAMING

BACKGROUND OF THE INVENTION

1. Field of the Invention

The present invention relates to implantable medical devices and methods, and more particularly to a pacing system and method for recording and reporting the occurrence of pacing events associated with the operation of an implantable pacemaker in combination with the respective rates of occurrence of such events.

One of the most common types of implantable medical devices in use today is the implantable pacemaker. Modern pacemakers are small, battery-powered electronic devices that monitor the activity of the heart to determine when the heart is naturally beating, and provide stimulation pulses to the heart when the heart is not naturally beating, thereby maintaining a prescribed heart rhythm or rate. Advantageously, a pacemaker may be implanted in a patient, and coupled to the patient's heart via appropriate pacemaker leads that are also implanted. By implanting the pacemaker and leads, the pacemaker becomes an integral part of the patient, and the patient is able to maintain a substantially normal life style without the bother and worry that typically accompany the use of external (non-implanted), life-sustaining medical devices.

Nearly all implantable pacemakers in use today, as well as similar implantable medical devices, can be configured by the attending physician in the physician's office. The process of configuring a pacemaker is commonly referred to as "programming." The programming process uses noninvasive telemetry to customize the operation of the pacemaker to fit the individual needs of the patient. Customization is achieved by adjusting a set of "pacemaker parameters" to values that cause the pacemaker to work in an optimum way for the particular patient within whom the device has been implanted.

Disadvantageously, as the complexity of new implantable devices has evolved over the past several years, it has become increasingly difficult for the attending physician, or other medical personnel, to determine how the pacemaker should be programmed in order to provide the most effective therapy for a given patient. This difficulty is particularly manifest with recent-generation pacemakers that tend to be more automatic and autonomous than earlier-generation pacemakers, which recent-generation pacemakers are controlled by input signals received from a multiplicity of internal sensors. For example, recent "rate-responsive" pacemakers provide stimulation pulses to a patient's heart, as needed, based on the input signals received from one or more physiological or other sensors that attempt to predict just how fast the patient's heart should beat in order to meet the patient's physiological needs.

A significant factor that makes the optimum programming of recent-generation pacemakers more difficult is the variation in each of the sensor inputs from patient to patient. Such variation is caused by numerous factors, including the patient's physical structure, the implant site, the particular disease or malady the patient has and its progression within the patient's heart or other body tissue, the drugs being taken by the patient to treat his or her condition, etc. Thus, to appropriately program the pacemaker for a given patient, the physician must anticipate how the pacemaker will operate given all of these variables, and given all the environments and activities that the patient is expected to encounter. Programming a modern pacemaker may thus comprise an extremely formidable task, for which task there is a critical need for programming aids to assist the physician in anticipating the pacemaker response for each particular patient.

It is known in the art to use programming aids and devices with implantable pacemakers to facilitate the physician's understanding of the pacemaker's programmed operation as its interacts with the patient's natural cardiac activity. For many years, the primary programming aid and source of diagnostic data for use in analyzing the operation of an implanted pacemaker has been the surface electrocardiogram (ECG), in which both pacemaker and heart activity are blended. From the ECG, the activity of the heart—including the contraction of the atria, the contraction of the ventricles, and the timing therebetween—could be displayed. From the pacemaker, the activity of the pacemaker—including when a heart contraction was sensed and when a stimulation pulse was generated—could likewise be monitored through the use of marker signals telemetered from the pacemaker to a remote (non-implanted) receiver, where such signals were processed and displayed as marks on the ECG waveform.

In recent years, specific programming devices have been developed that not only allow the pacemaker parameters to be noninvasively set to desired values, but that also allow the operation of the pacemaker and the heart to be monitored without having to obtain a surface ECG. Such is accomplished by transmitting an intracardiac ECG signal, either alone or in combination with marker signals. See e.g., U.S. Pat. Nos. 4,559,947; 4,596,255; 4,791,936; and 4,809,697.

Unfortunately, while such prior art programming devices have done much to facilitate communications with and analysis of implantable programmable pacemakers, they all suffer from one major drawback—they are limited to real-time data analysis. This is true even though some provide the capability of capturing a short segment, e.g., 30 seconds, of the intracardiac ECG signal, which intracardiac ECG signal, once captured, can advantageously be expanded, compressed, or otherwise processed in a desired manner in order to better examine it. Unfortunately, in order to properly assess some types of problems that may develop for a given patient having an implanted pacemaker, it is frequently necessary to examine the intracardiac signal, or at least the main components thereof, over a much longer period of time, e.g., days, weeks, or months. What is needed, therefore, is not only a programming device that facilitates the physician's ability to understand the interaction of the implanted device with the patient and to evaluate active clinical problems, but also a device that allows the physician to assess the performance of the system over an extended period of time, e.g., on the order of days, weeks, or months.

The commonly used solution to the above-described problem is to use a Holter Monitor, or equivalent external device. A Holter Monitor is essentially a recorder that is carried by the patient. The Holter Monitor senses the surface ECG signal and records it. Thus, after the data-collection period during which the Holter Monitor is used (usually 24 hours), the number of specific cardiac events that occurred, e.g., the number of ventricular contractions, may be determined.

Disadvantageously, Holter Monitors, and equivalent devices, are external devices that must be carried by the patient continuously throughout the monitoring period. Such carrying can be a nuisance and a bother to the patient. Further, such externally-carried recording devices suffer from numerous limitations. One of the main limitations is their inability to consistently identify the high-frequency pacing stimulus generated by the pacemaker. This is particularly the case when the pacemaker generates a bipolar pacing pulse, which pacing pulse is of relatively low amplitude and difficult to detect (compared to a unipolar pacing pulse). Thus, although the contraction of the heart may be recordable, there is no way of easily determining whether the contraction was a natural contraction or a paced contraction. Further, if a pacing pulse is generated and the heart does not respond to it (i.e., if there is a lack of "capture"), such event is not detectable.

Another limitation of Holter Monitors, and equivalent externally-carried recording devices, is that they have no way of monitoring, and hence recording, the internal state of the implanted pacemaker. A knowledge of the internal state of a pacemaker would be invaluable in determining the actual pacemaker behavior. Advantageously, the implanted pacemaker "knows" exactly when it paces and senses on each channel and how it is responding to every input signal. Thus, what is needed is an implanted pacemaker that is equipped to track and report its behavior over time; and, upon command, provide such information to an attending physician.

There are at least two prior art devices known to the inventors that attempt to address the above needs. On such device is the Cosmos TM 283-01 pacemaker marketed by Intermedics, Inc. of Angleton, Tex. The Cosmos 283-01, using a feature termed "Diagnostic Data TM," counts the number of specific cardiac events that occur during the monitoring period. See, Sanders et al., "Data Storage and Retrieval by Implantable Pacemakers for Diagnostic Purposes," PACE. Vol. 7, pp. 1228-33 (1984); and Levine, P. A., "Diagnostic Data: An Aid to the Follow-Up and Assessment of the Pacing System," *Journal of Electrophysiology*, Vol. 1, pp. 144-53 (1987). The other device is the CHORUS TM 6033 pacemaker marketed by ELA Medical, of Montrouge, France. Both of these devices, and similar devices described in the literature, see, e.g., U.S. Pat. No. 4,513,743 (van Arragon et al.), are thus able to determine the total number of occurrences of a selected cardiac event, e.g., the number of times that an atrial pulse is issued; or the number of times that an atrial-to-ventricular (AV) interval has a delay that falls within defined time limits. Disadvantageously, however, such devices do not record the frequency of occurrence of the cardiac events that are counted. This limitation prevents many necessary evaluations from being performed, such as the determination of sensor responsiveness and an assessment of chronotropic competence. What is needed, therefore, is an implantable medical device that not only detects and records the occurrence of specified cardiac events, and in particular pacemaker events or states, but that also determines and records the frequency of occurrence, or the rate, associated with each such detected and recorded event.

The present invention advantageously addresses the above and other needs.

SUMMARY OF THE INVENTION

The present invention includes a means for monitoring the behavior of an implanted pacemaker by counting (recording) the number of times that a given internal event or state change of the pacemaker occurs, and associating a rate with each event or state change thus counted (recorded). The event counts and their associated rate (where the "rate" of a particular event count is the frequency, within specified ranges, at which the particular event count occurs) are stored (recorded) in appropriate memory elements housed within the pacemaker device as event/rate data. At an appropriate time, such event/rate data is downloaded to an external programming device through a conventional noninvasive telemetry communication link established between the implanted pacemaker and the external programming device. The external programming device then processes the event/rate data, and displays a distribution of the event count data as a function of its rate of occurrence, as well as other statistical information derived therefrom, in an easy-to-understand format.

Advantageously, the display of the distribution of the event/rate data, and its associated statistical information, allows a baseline recording to be performed that establishes the implanted pacemaker's behavior for a given patient under known conditions. The conditions are known because they are past conditions. Such baseline recording of the pacemaker event counts in combination with the associated rate of occurrence of such event counts provides significant insight into the past behavior of the pacemaker as implanted in a particular patient. The past behavior of the pacemaker, in turn, advantageously provides a way to predict with a high degree of accuracy the future behavior of the pacemaker for the particular patient under similar conditions.

One aspect of the invention thus provides a programming aid or tool that allows a physician to better anticipate how an implanted pacemaker, programmed to operate in a specific mode, will respond for a particular patient. Advantageously, such programming aid provides sufficient detailed information to enable the physician to readily and accurately analyze and predict the expected behavior of the implanted pacemaker when programmed in a certain manner for the particular patient within whom the pacemaker is implanted. Once such detailed and patient-specific information is known, selecting the optimum "pacemaker parameters" to be programmed into the pacemaker becomes a relatively straightforward and easy task.

Another aspect of the invention provides a pacing system wherein an event histogram is created. Advantageously, such event histogram provides more than just event counts sorted or classified into "bins" by type, as do histograms of the prior art. Rather, the event histogram of the present invention keeps track of each pacing event in both an appropriate event "bin," and an appropriate rate "bin." Such collection of both event counts and event rates offers numerous advantages. For example, having available both an event count and an event rate allows the number of paced events that are paced under sensor drive (i.e., as controlled by a physiological sensor coupled to the pacemaker when the pacemaker is configured to operate as a rate-responsive pacemaker) and the actual rates that have been achieved to be identified. Such data also makes it feasible for a physician to readily assess chronotropic function, as well as to gain insight into the appropriate atrial-to-ventricular (AV) interval and other selected programmed parameters that should be employed for a particular patient. Such data further makes it possible to detect atrial undersensing and the frequency of ventricular ectopy or oversensing. Moreover, the percent of paced events that are atrial paced and ventricular paced can be readily determined, as can the total amount of time which the pacing system has spent at the programmed maximum tracking rate.

In accordance with yet another aspect of the invention, at least five pacing states associated with the operation of a dual-chamber pacemaker are reported. These are: (1) an atrial stimulation pulse (A-pulse) followed by a ventricular stimulation pulse (V-pulse), referred to as an "AV" event; (2) an A-pulse followed by an R-wave (a natural ventricular contraction) sensed in the ventricle, referred to as an "AR" event; (3) a P-wave (a natural atrial contraction) sensed in the atrium followed by a V-pulse, referred to as a "PV" event; (4) a P-wave followed by an R-wave, referred to as a "PR" event; and (5) a premature ventricular event, referred to as a "PVE," and defined as a sensed R-wave with no previously sensed P-wave or A-pulse. In addition, two other events may also be reported in some embodiments of the invention. They are: (6) a P-wave sensed during the maximum tracking rate (MTR) interval, followed by a V-pulse, and referred to as a "P@MTR-V" event; and (7) a P-wave sensed during the MTR interval, followed by a sensed R-wave, and referred to as a "P@MTR-R" event. Advantageously, the occurrence of all of these reported events may be readily ascertained by simply monitoring the state changes of the implantable pacemaker.

It is thus a feature of the present invention to provide a programming tool or aid that facilitates a physician's ability to understand the interaction of an implanted medical device, such as a pacemaker, with a particular patient so that the physician can better evaluate active clinical problems, and to also provide a tool or aid that facilitates the physician's ability to assess the performance of the implanted medical device over an extended period of time, e.g., on the order of days, weeks, or months.

It is another feature of the invention to provide a summary report of the number of complexes that occur in each of a plurality of pacing states, as well as a distribution of the various rates within each pacing state. (Note, as used herein the term "complexes" means identifiable events in the cardiac/pacemaker cycle, e.g., P-waves, R-waves, A-pulses, and V-pulses, PVE's, etc., or specified combinations of such events.)

It is still another feature of the invention to provide an implantable medical device, such as a pacemaker, that is equipped to track and report its behavior over time; and, upon command, provide such information to an attending physician.

It is an additional feature of the invention to provide an implantable medical device that not only detects and records the occurrence of specified events, and in particular pacemaker events or states, but that also determines and records the frequency of occurrence, or the rate, associated with each such detected and recorded event.

It is a further feature of the invention to provide a system and/or method for reporting and displaying the event counts associated with the operation of an implantable medical device that indicates the distribution of such event counts over time.

It is yet an additional feature of the invention to provide a reporting system for use with an implantable pacemaker and an external programmer device that includes dedicated recording circuitry within the implantable pacemaker to record the occurrence and rate of specified pacing events, and processing circuitry in the external programmer that is programmed to retrieve, process and display the information recorded in the pacemaker in a way that allows a physician to optimally program the operating parameters of the implantable pacemaker for a particular patient.

It is yet a further feature of the invention to display pacing data accumulated over a specified time period in an event histogram and/or an event rate table.

BRIEF DESCRIPTION OF THE DRAWINGS

The above and other aspects, features and advantages of the present invention will be more apparent from the following more particular description thereof, presented in conjunction with the following drawings wherein:

FIG. 2 is a block diagram of the pacemaker of FIG. 1 and illustrates how an external programmer is used therewith;

FIG. 19 is a typical Event Histogram printout as generated by the external programmer in accordance with the present invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Before describing the reporting and displaying features associated with the present invention, it will be helpful to review the main components of a pacing system, i.e., the pacemaker and the programmer, and to provide an overview of their operation.

The Pacemaker

Figure 1:
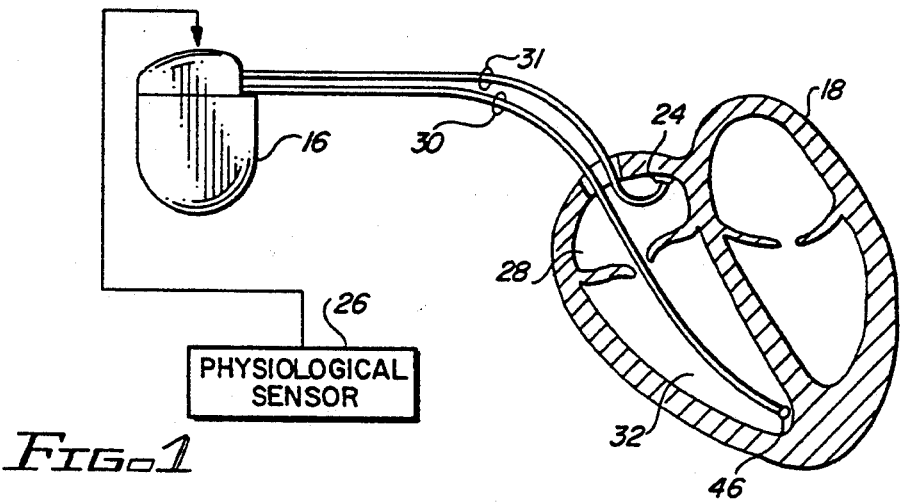
FIG. 1 shows an implantable pacemaker having a physiological sensor coupled to a heart.

The pacemaker side of a pacing system is shown in FIG. 1. As seen in FIG. 1, an implantable pacemaker 16 has a physiological sensor 26. Although a sensor 26 is shown coupled to the pacemaker 16, it is to be understood that the present invention may be used with pacemakers that do not have a sensor 26 coupled thereto, or to pacemakers wherein such a sensor has been programmed to an OFF or PASSIVE mode. The pacemaker 16 is coupled to a heart 18 by way of pacing leads 30 and 31. The pacing lead 30 has an electrode 46 positioned in the right ventricle 32 of the heart 18. The lead 30 is thus typically referred to as the ventricular lead, and the signals generated by the pacemaker for delivery to the heart through electrode 46 over lead 30, or the signals sensed through electrode 46 and the lead 30, are processed by circuits in what is known as the ventricular channel of the pacemaker 16. Similarly, the pacing lead 31 has an electrode 24 positioned in the right atrium 28 of the heart 18. The lead 31 is thus typically referred to as the atrial lead, and the signals generated by the pacemaker for delivery to the heart through the electrode 24 over lead 31, or the signals sensed through electrode 24 and the lead 31, are processed by circuits in what is known as the atrial channel of the pacemaker 16.

Note that what is shown in FIG. 1 is a dual-chamber pacemaker, in that sensing and/or pacing may occur in both chambers of the heart 18, i.e., in the atrium 28 and/or the ventricle 32. It is to be understood that the present invention may be used with either dual-chamber pacing, as shown in FIG. 1, or with single-chamber pacing, where sensing and pacing occur in only one chamber of the heart. It should also be understood that most pacemakers that provide a dual-chamber configuration, such as is illustrated in FIG. 1, may also be programmed to operate in a single-chamber mode.

Referring next to FIG. 2, a more detailed block diagram of the dual-chamber pacemaker 16 is shown. Note that as shown in FIGS. 1 and 2, the atrial lead 31 and the ventricular lead 30 are unipolar leads. In unipolar operation, the tip electrode 24 or 46 provides one signal path, with the return signal path being provided through conductive body tissue and fluids to an exposed portion of the pacemaker case 64. It is to be understood, however, that either one or both of the leads 30 or 31 could be bipolar leads, having two electrodes, in which case the signal return path is provided through the other electrode (which other electrode is typically a ring electrode that is positioned only a few centimeters from the tip electrode).

As suggested in FIG. 2, the pacemaker 16 is in telecommunicative contact with an external programmer 20 via a telemetry link 70. The programmer 20 includes a telemetry receiver and monitor external to the patient's skin 21. The pacemaker 16 includes a telemetry subsystem 40 for transmitting data and parameter values to the external telemetry transmitter and receiver of the external programmer 20, and for receiving data instructions and the like from the external programmer 20. Data instructions received from the external programmer 20 are decoded in decoder and encoder 60 and stored in memory 62. Likewise, data and parameter values to be sent to the external programmer 20 are encoded in the decoder and encoder circuit 60 prior to transmission. The manner of establishing and operating a telemetry link between an external programmer and implantable medical devices is known in the art.

The data instructions stored in the memory 62 control the operation of the pacemaker. In particular, the stimulation pulses generated by the pacemaker are generated in pulse output circuits 44 as triggered by appropriate trigger signals obtained from the pacemaker state logic and related circuitry 42. The state logic circuitry 42 defines a plurality of operating states for the pacemaker 16 as a function of various timing signals generated by the pacemaker timer circuits 50 and/or various other signals or conditions sensed through the atrial, ventricular, or telemetry channels of the pacemaker 16. For example, at the conclusion of an appropriate timing interval, typically referred to as the atrial escape interval, the state logic 42 changes to a particular state that causes an atrial stimulation pulse (A-pulse) to be generated by the pulse output circuits 44 and delivered to the atrium 28 through the electrode 24 via the atrial lead 31. In a similar manner, the state logic 42 changes to another particular state that causes a ventricular stimulation pulse (V-pulse) to be generated at the conclusion of another timing interval, typically referred to as the ventricular escape interval, which V-pulse is delivered to the ventricle 32 through the electrode 46 via the ventricular lead 30.

When operating in a demand mode, stimulation pulses are provided as above described only in the absence of natural cardiac activity, i.e., only when the heart 18 is not beating (contracting) on its own. Natural cardiac activity is determined by monitoring the leads 30 and/or 31 for electrical activity indicative of muscle contraction. Atrial contraction is manifest by the presence of a P-wave sensed through the atrial tip electrode 24 and the atrial lead 31 through amplifier 48. Similarly, ventricular contraction is manifest by the presence of an R-wave sensed through the ventricular tip electrode 46 and the ventricular lead 30 through amplifier 46. Thus, the occurrence of a P-wave, for example, causes the state logic 42 to immediately assume a different state, which state restarts the atrial escape interval timer in the pacemaker timer circuits 50, and thus inhibits an A-pulse from being generated. In like manner, the occurrence of an R-wave causes the state logic 42 to assume yet another state, which state restarts the appropriate time intervals in the pacemaker timer circuits, and inhibits a V-pulse from being generated.

The physiological sensor 26 (usually referred to as just the "sensor") senses an appropriate physiological parameter, such as physical activity, blood oxygen level, respiration rate, etc. The physiological parameter thus sensed is indicative of how fast the heart 18 should be beating. That is, in times of high physiological stress, such as a high physical activity level, the heart needs to beat at a much faster rate in order to provide an adequate blood supply to the patient's body. Contrariwise, in times of low physiological stress, such as a very low physical activity level (e.g., when the patient is sleeping), the heart may beat at a much slower rate. Thus, in a pacemaker programmed to operate using the physiological sensor 26, the state logic 42 receives a signal 53 generated by the sensor 26 (generally referred to as the "sensor input signal," because it is the signal that is "input" to the pacemaker 16 from the sensor 26), processes the signal 53 in an appropriate manner, and uses the processed result to alter or adjust the basic time intervals of the pacemaker so that the pacemaker will provide stimulation pulses on demand at a faster or slower rate, as needed. Such a pacemaker 16, i.e, one that is capable of adjusting the rate that stimulation pulses are provided on demand as a function of one or more sensed physiological parameters, is known as a "rate-responsive pacemaker." It is further noted that the present invention has applicability to rate-responsive pacemakers, as well as non-rate-responsive pacemakers.

It is also noted that the pacemaker state logic 42, and the pacemaker timer circuits 50, while shown as separate blocks in the block diagram of FIG. 2, may be realized using a microprocessor circuit 52 controlled by an appropriate programmed set of instructions in the memory 62. In fact, the preferred manner of implementing the pacemaker 16 is to use a microprocessor 52 in combination with appropriate logic circuitry as described in U.S. Pat. No. 4,940,052, which patent is incorporated herein by reference.

In general, the states defined by the pacemaker state logic 42 may be as summarized below in Table 1 is taken from the '052 patent, cited above, and much of the terminology used in Table 1 is further explained in that patent. Note from Table 1 that the entire operation of the pacemaker 18 may be controlled by defining some 18 states.

TABLE 1

States of Pacemaker State Logic

| State | Symbol | Description |
|---|---|---|
| 0 | APW | A Pulse |
| 1 | BLANK | V Sense Input Inhibit (Blank) |
| 2 | AREF | A Refractory |
| 3 | SIPW | Sensed Inhibiting P Wave |
| 4 | AVD | A-V Delay |
| 5 | CROSS | Crosstalk Sense |
| 6 | VPW | V Pulse |
| 7 | SIRW | Sensed Inhibiting R Wave |
| 8 | VAD | V-A Delay |
| 9 | SHORT1 | Shorten A-V Delay 50 msec if IPW during SHORT1 with Physiologic A-V Delay on |
| A | MTR | Maximum Track Rate — Shorten A-V Delay 25/75 msec and Delay IPW until MTR end if P wave sensed during MTR; 75 msec if Physiologic A-V Delay on |
| B | SHORT2 | Shorten A-V Delay 75 msec if IPW during SHORT2 with Physiologic A-V Delay On |
| C | RRT | Lengthen V-A internal if at low battery |
| D | RNOISE | R Noise sensed during VREF or RNOISE |
| E | LIPW | Latched IPW -- P wave sensed in MTR |
| F | PNOISE | P Noise sensed furing AREF or PNOISE |
| (none) | VREF | V Refractory, independent 1-bit state machine synchronized to PGSL when AREF starts |
| (none) | ABSREF | 108 msec Absolute Refractory starts when AREF starts |

The External Programmer

Figure 3:
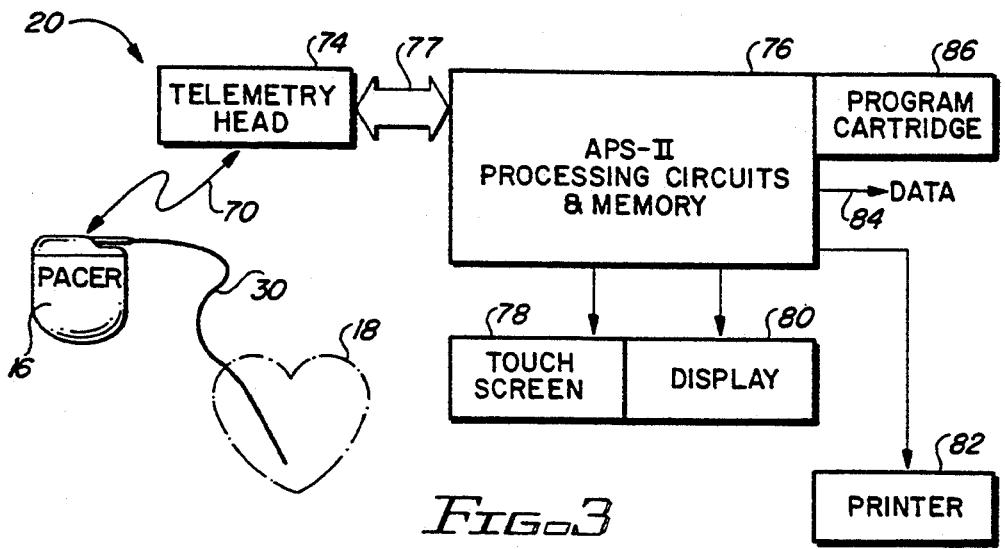
FIG. 3 is a simplified block diagram of an external programmer that may be used with an implantable pacemaker in accordance with the present invention.
Figure 4:
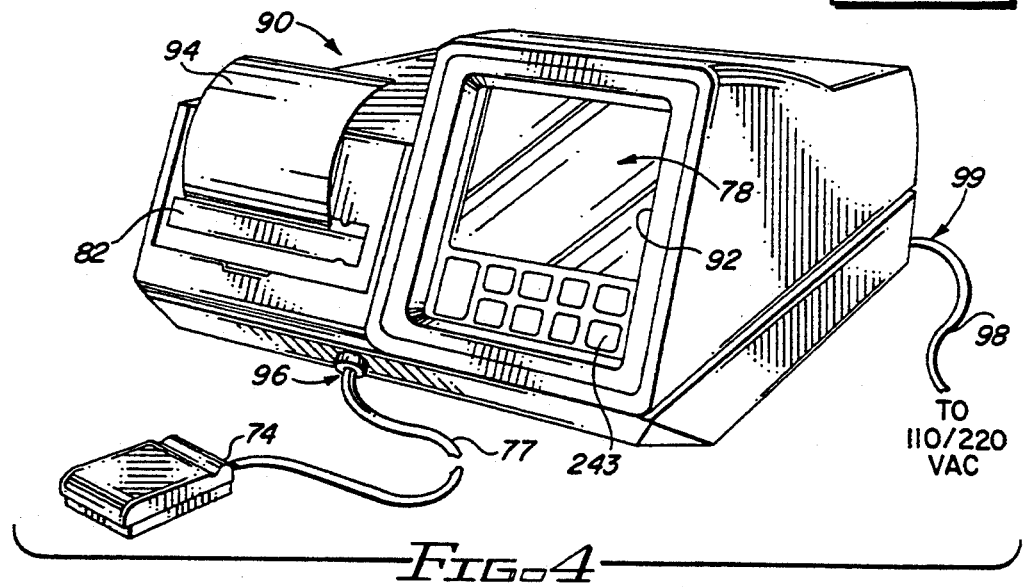
FIG. 4 is a perspective view of the external programmer of FIG. 3.

It is noted that FIGS. 1 and 2, as described above, relate primarily to the pacemaker side of a pacing system 16. However, as noted above, the external programmer side of a pacing system also plays a key part of the invention. Hence, a brief overview of the external programmer 20 used with the present invention will next be presented. Such brief overview will be made in connection with FIGS. 3 and 4. FIG. 3 shows a block diagram of an external programmer 20 usable as part of the present invention, while FIG. 4 shows a perspective view of the external programmer of FIG. 3. A more complete description of the external programmer 20 may be found in U.S. Pat. No. 4,809,697, which patent is also incorporated herein by reference.

The external programmer 20 used with the present invention is hereafter referred to as an analyzer-programmer system (APS). A preferred APS is the APS-II/MTM, manufactured and sold by Siemens Pacesetter, Inc., of Sylmar, Calif. The APS-II/MTM provides a sophisticated, microprocessor-based programming system that can be used to noninvasively interrogate and program the programmable, implantable pacemakers manufactured by Siemens Pacesetter, Inc. However, while the APS-II/MTM represents the preferred embodiment and best mode of the programmer 20, it is to be understood that other models and types of external programmers can and will exist with which the present invention may be used. It is further noted that some of the processing and display features of the APS-II/MTM are described in U.S. Pat. No. 4,791,936, also incorporated herein by reference.

Turning now to FIG. 3, a very simplified block diagram of the APS-II/MTM is presented. The programmable pacemaker 16, presumably implanted within living tissue, is in electrical contact with the heart 18 via at least one pacemaker lead 30. (It is noted that while the pacemaker 16 in FIG. 3 is presumed to be implanted in a patient, it need not be implanted for the APS-II/MTM to function. For example, for training purposes, it is quite common to use an APS-II/MTM with a non-implanted pacemaker that is coupled to a heart simulator.)

As described above in connection with FIGS. 1 and 2, the pacemaker 16 is a self-contained unit capable of both sensing natural cardiac activity (P-waves and/or R-waves) and providing stimulation pulses (A-pulses and/or V-pulses) to invoke paced cardiac activity. The operating characteristics of the pacemaker 16 can be noninvasively programmed by way of command signals received over telemetry link 70, which command signals are received from a telemetry head 74 connected to the APS-II/MTM processing circuits 76 by way of a connection cable 77. The command signals are generated within the APS-II/MTM processing circuits 76 as a function of operating commands received by way of a touch sensitive screen 78. That is, an APS-II/MTM operator selects a desired command by touching a designated area on the touch screen 78, which designated area is defined by a particular pattern displayed on a display screen 80. Advantageously, the touch screen 78 overlays the display screen 80 so that all one need do to make a command selection is to touch the screen at the area indicated on the display for the desired command.

The pacemaker 16 is also capable of sending operating data and measured data over the telemetry link 70 to the telemetry head 74. Such measured data includes event histogram/rate data as described more fully below, which event histogram/rate data is determined by monitoring particular changes in state of the pacemaker state logic 42. The telemetry head 74 preliminarily processes such data and forwards it on to the APS-II/MTM processing and memory circuits 76. Data received at the APS-II/MTM circuits 76 may be displayed on the display screen 80, printed on a printer 82, and/or stored within the memory elements of the APS-II/MTM circuits 76 for subsequent retrieval and display. Alternatively or conjunctively, data received at the APS-II/MTM circuits 76 may be transmitted over an appropriate data channel 84 to a desired external device, such as a modem, an X-Y plotter, a tape or disk drive, a personal computer, or other peripheral device.

Operation of the APS-II/MTM processing and memory circuits is controlled by way of a program cartridge 86 that is detachably connected to the processing and memory circuits 76. Removable program cartridge 86 thus advantageously allows the operating characteristics of the APS-II/MTM device to be easily upgraded to include new features and to properly interface with new pacemakers, as new features and new pacemakers are developed. Such upgrading can occur at minimal cost because all that is required is a new program cartridge 86, rather than a whole new analyzer-programming system 20, as has been required in the past. The present invention, relating to a method and system for recording and reporting the distribution of pacing events over time, is facilitated through the use of a such new program in a new program cartridge 86.

Figure 17:
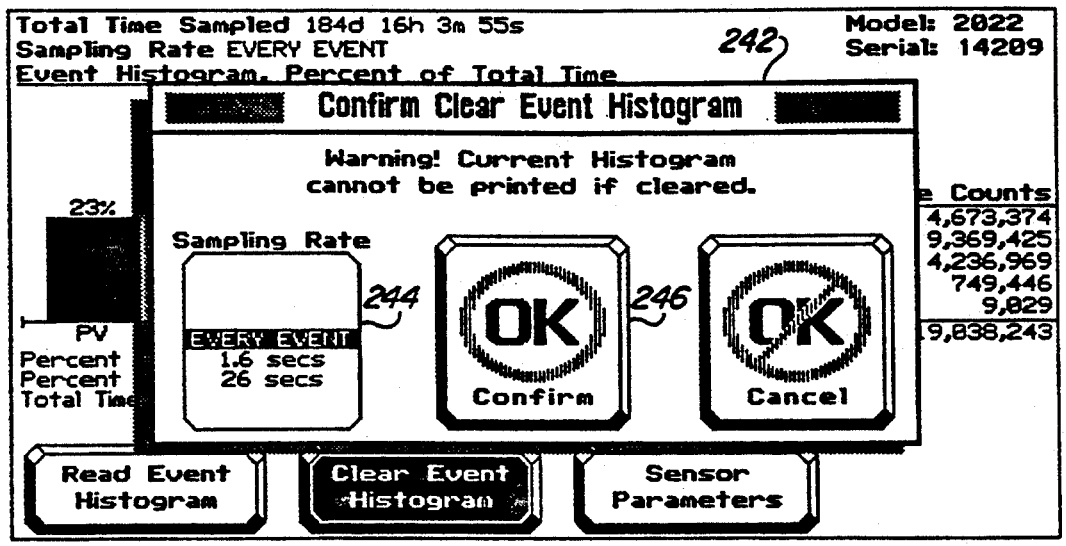
FIG. 17 shows a popup screen that is used by the external programmer to clear the Event Histogram and clear the event counter data.

FIG. 4 illustrates a housing 90 within which the APS-II/MTM system components are housed. In accordance with one embodiment, all of the circuits of the APS-II/MTM processing circuits and memory 76, including the printer 82, the display screen 80, the touch screen 78, and the program cartridge 86, are housed within the housing 90. The telemetry head 74 is coupled to the housing 90 by way of cable 77. As seen in FIG. 17, a CRT screen 92, over which touchscreen 78 is laid, provides a readily visible and accessible means for viewing displays and selecting commands. Similarly, the printer 82 provides a paper copy 94 of that which is displayed on the screen of the CRT 92, or other desired information, as selected by the various commands available through touching the touchscreen. The telemetry head module 74 is attached to cable 77 which plugs into a connector 96 located on the bottom front side of the housing 90. A power cord 98 similarly plugs into socket 99 at the rear of the housing and allows the APS-II/MTM to be powered from any suitable electrical outlet providing 110/120 VAC at 60 Hz. The power cord 98 may be stored on the bottom of the housing 90 for ease of transportation and storage. Similarly, the telemetry head 74, when detached, can be stored in a removable front cover (not shown) when not in use.

Gathering the Event Histogram Data

Figure 5:
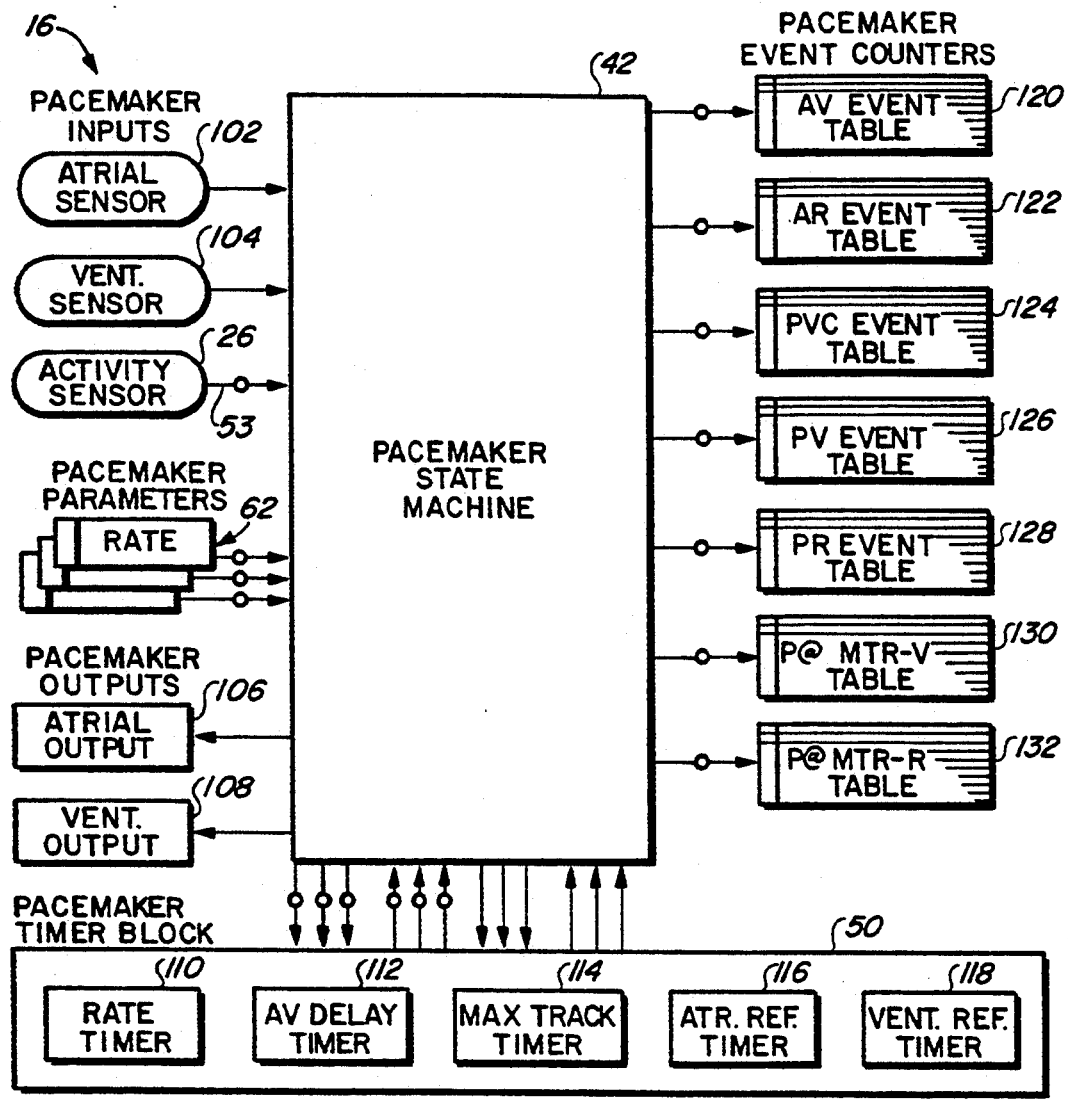
FIG. 5 is a functional block diagram of the pacemaker of FIG. 2, showing event counters coupled to the pacemaker state machine.

With the above overview in mind of both the pacemaker 16 and the external programmer 20 of a representative pacing system, reference is next made to FIG. 5 where there is shown a functional block diagram of the pacemaker 16 that highlights the key elements used with the present invention. As with all the figures used herein, like reference numerals are used in FIG. 5 to describe like parts used in other figures. Thus, shown in FIG. 5 is the pacemaker state logic 42, referred to as the pacemaker state machine. Also shown in FIG. 5 is the pacemaker timer circuits 50, referred to as the pacemaker timer block. The pacemaker inputs, i.e., signals sensed by the pacemaker that are not programmed, include an atrial sensor 102 and a ventricular sensor 104 that sense P-waves and R-waves, respectively. For example, the atrial sensor 102 may be made up of the atrial tip electrode 24, atrial lead 31 and atrial channel amplifier 48 as shown in FIG. 2. Similarly, the ventricular sensor 104 may be made up of the ventricular tip electrode 46, the ventricular lead 30 and the ventricular amplifier 56 shown in FIG. 2. The pacemaker inputs also include the sensor input signal 53 obtained from the physiological sensor 26. (It is noted that while only a single physiological sensor 26 is shown in FIGS. 1, 2 and 5, more than one such sensor may be used, each providing its own sensor input.)

In addition to the above-described pacemaker inputs, there are several pacemaker parameters that are input to the pacemaker state machine in order to control its operation in a desired fashion. Such parameters are normally programmed into the memory 62 of the pacemaker 16 using the appropriate telemetry link 70. Such parameters include, e.g., the programmed rate at the which the stimulation pulses are to be generated by the pacemaker, the particular mode of operation of the pacemaker, and the like.

The pacemaker outputs, i.e., signals generated by the pacemaker state machine 42 in response to the pacemaker inputs and/or pacemaker parameters include an atrial output 106 and a ventricular output 108. The atrial output 106 provides an A-pulse for delivery to the atrium at an appropriate time, e.g., on demand as needed to maintain a programmed or sensor-indicated heart rate. The ventricular output 108 similarly provides a V-pulse for delivery to the ventricle at an appropriate time, e.g., on demand as needed to maintain a programmed or sensor-indicated heart rate.

The pacemaker timer circuits 50 include at least five separate timers. A rate timer 110 measures the pacing cycle duration. An AV Delay Timer 112 defines the time period between an A-pulse and a V-pulse. A Max Track Timer 114 defines the time period of the maximum rate at which the pacemaker is allowed to provide stimulation pulses, i.e., it defines the maximum track rate (MTR). An Atrial Refractory Timer 116 defines the atrial refractory period (i.e., that time period during which the atrial channel is refractory). Similarly, a Ventricular Refractory Timer 118 defines the ventricular refractory period, or that time during which the ventricular channel is refractory.

Note from the symbols used in FIG. 5 that two kinds of data are passed to and from the pacemaker state machine 42. Such data may take the form of a trigger signal or a parameter signal. A trigger signal, represented by an input line with an arrow pointing the direction of flow of the trigger data, is a signal that operates substantially immediately, much like an interrupt signal, to bring about a desired result. That is, for example, immediately upon sensing atrial activity through the atrial sensor (or within one or two clock cycles thereafter, where a clock cycle is typically on the order of a few microseconds), the state of the state machine 42 changes appropriately to bring about a desired result. In contrast, a parameter signal, represented by an input line passing through a circle with an arrow pointing the direction of flow of the parameter data, is a signal that is made available to the indicated element for use at the appropriate time during the normal timing cycle of the state machine. That is, for example, at the appropriate time in the normal state machine timing cycle, the "MTR" parameter is transferred to the timer 114 so that the appropriate period of the maximum track rate may be defined.

As indicated above in Table 1, there are some eighteen states associated with the operation of the pacemaker 16 when configured for operation in a dual-chamber mode. Three of the eighteen defined states relate directly to cardiac activity that occurs in the atrium. These three atrial states are: (1) atrial pulse (A-pulse), referred to as "APW" or state 0 in Table 1; (2) sensed P-wave, referred to as "SIPW" or state 3 in Table 1; and (3) sensed P-wave during the Maximum tracking interval, referred to as "LIPW," or state E in Table 1. Similarly, two of the eighteen defined states relate to cardiac activity that occurs in the ventricle. These two ventricle states are: (1) ventricular stimulation pulse (V-pulse), referred to "VPW," or state 6 in Table 1; and (2) sensed R-wave, referred to as "SIRW," or state 7 in Table 1. Advantageously, the changing of the state machine 42 from one state to another state signals the occurrence of a particular event. Selected state changes associated with the state machine 42 may thus be considered as "pacing events." In accordance with the present invention, such "pacing events are recorded as a function of the type of event that occurred, and as a function of the rate of occurrence of such event.

There are four basic pacing event types that are recorded by the present invention. These are: (1) a P-wave followed by a V-pulse (referred to as a "PV" event); (2) a P-wave followed by an R-wave (referred to as a "PR" event); (3) an A-pulse followed by a V-pulse (referred to as an "AV" event); and (4) an A-pulse followed by an R-wave (referred to as an "AR" event). Note from Table 1 that a PV event occurs when the state machine 42 changes from state 3 to state 6. Similarly, a PR event occurs when the state machine changes from state 3 to state 7; an AV event occurs when the state machine changes from state 0 to state 6; and an AR event occurs when the state machine changes from state 0 to state 7.

To the above four basic pacing event types, three other pacing events may be defined for purposes of the present invention. These other three pacing event types are: (5) a premature ventricular event (referred to as a "PVE"); (6) a P-wave at the maximum tracking rate followed by a V-pulse (referred to as a "P@MTR-V" event); and (7) a P-wave at the maximum tracking rate followed by an R-wave (a "P@MTR-R" event). A premature ventricular event is defined as an R-wave that occurs without an appropriate intervening atrial event. With respect to the states defined in Table 1, a PVE may thus occur when the state machine 42 changes from state 8 (which may be initiated after state 6 or state 7) back to state 7. (In a non-PVE sequence, state 8 would normally be followed by state 0 or state 3.) A P@MTR-V event occurs when the state machine changes from state E (LIPW) to state 6 (VPW). Similarly, a P@MTR-R event occurs when the state machine changes from state E to state 7 (SIRW).

It is noted that if only single-chamber pacing is employed, then the pacing events that are counted, and their respective rates, are simply "sensed events" and "paced events."

Because the pacing events defined above are reflected in prescribed state changes of the state machine 42, the occurrence of such events may be readily determined by simply monitoring the state machine for the prescribed state changes. In particular, in accordance with the present invention, the occurrence of any of the above-defined seven pacing events are counted in appropriate pacemaker event counters as a function of rate of occurrence, as shown in FIG. 5. Thus, for example, an AV event table 120 is maintained that keeps track of (i.e., counts) each AV event that occurs. The AV events are tracked in a "table," as opposed to a "counter" because such events are tracked as a function of rate, as well as occurrence. That is, each occurrence of an AV event is logged into the AV event table 120 in an appropriate cell corresponding to the particular frequency or rate of occurrence of the AV event. Thus, the AV event table 120 may be considered as an array of AV event counters, with each counter in the array being assigned a particular rate range, as explained more fully below in connection with FIG. 6.

In a similar manner, an AR event table 122 is maintained to keep track of each AR event that occurs. Likewise, other tables are maintained to keep track of each PVE (table 124), each PV event (table 126), each PR event (table 128), each P@MTR-V event (table 130), and each P@MTR-R event (table 132).

Figures 6, 11:
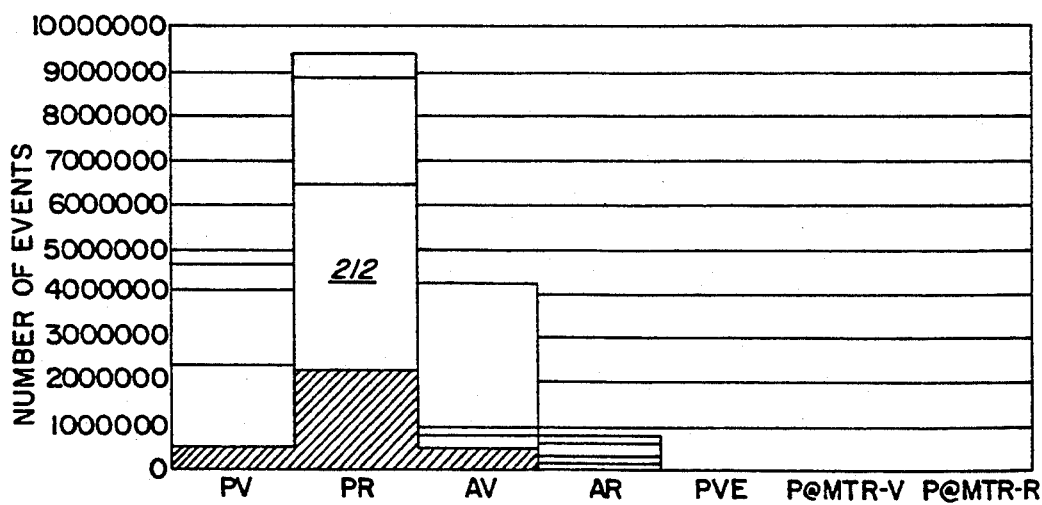
FIG. 6 illustrates typical event counter histogram data that is accumulated by the event counters of FIG. 5 as a function of rate in accordance with the present invention.
FIG. 11 shows additional information that may be derived from the event counter data of FIG. 6.

The event tables 120-132 are maintained in the memory 62 of the pacemaker 16. In accordance with the present invention, the count data stored in such tables may be organized into an event histogram 140 as illustrated in FIG. 6. As seen in FIG. 6, the event histogram 140 defines a plurality of rates, expressed as a function of pulses per minute (ppm), along one side of the event histogram. The pacing events being tracked are listed along the other side of the event histogram 140. For the event histogram 140 shown in FIG. 6, for example, the rates are defined in the left column, and the pacing event types are defined across a top row. (Such definition could, of course, be reversed, if desired, placing the event types as a column and the event rates as a row.) Each column of the event histogram shown in FIG. 6 thus corresponds to one of the "event tables" of FIG. 5, and reference numerals have been added at the top of each column in FIG. 6 to show this correspondence.

Thus, as seen in FIG. 6, the pacing events are counted as a function of rate by sorting each pacing event as a function of rate, and then incrementing a count held in the appropriate cell of the event table that corresponds to the particular event type that occurred. For example, as indicated in FIG. 6, during the time period during which the pacing event/rate data was collected, there were 0 PV events that occurred at a rate of between 0-60 ppm, yet there were 583,335 PV events that occurred at a rate of between 61-67 ppm, and 1,689,030 PV events that occurred at a rate of between 68-75 ppm. In contrast, there were 3,257,853 AV events that occurred at a rate of between 0-60 ppm, 55,493 AV events that occurred at a rate of between 61-67 ppm, and 101,970 AV events that occurred at a rate of 68-75 ppm. In a similar manner, the number of pacing events of each type that occurred within one of the identified rate ranges is indicated in an appropriate cell of the respective event tables maintained in the pacemaker memory 62.

A key feature of the present invention is that the pacing event/rate data stored in the event Tables 126-132 may be stored as every pacing event occurs, or on a sampled basis. Two sampling rates, in addition to an "every event" rate, may be used: e.g., 1.6 seconds or 26 seconds. If a sampled rate is used, then a sample interval timer within the timer block 50, or equivalent timing function, causes the most recent pacing event (of the seven possible pacing events) to be stored in appropriate rate cells in the event Tables 126-132 at the conclusion of the sampling period. The use of a sampling period thus allows a significantly longer monitoring period before the available memory for the event histogram fills up.

Given the event/rate organization of the event Tables 126-132, appropriate circuitry within the pacemaker 16, and particularly within the memory 62 of the pacemaker 16, may be readily fashioned to monitor and count the pacing event data. In applicants' preferred embodiment, 192 bytes of the pacemaker memory 62 are allocated for the storage of the event/rate data.

Appropriate commands received from the external programmer 20 allow the event/rate data to be cleared, or downloaded to the external programmer. A two-bit code held in a designated location of the memory 62 specifies whether the sampling rate is every event (code 00), every 1.6 seconds (code 10), or every 26 seconds (code 10). Event designators are used to represent each event type that is monitored. Such event designators are simply 3-bit values in the range of 0-7. The event designator for the pacing events monitored by the present invention are defined in Table 2.

The memory allocated to the event/rate data is organized primarily according to ranges of pacing cycle time, or current pacing rate, which is in effect the time of each event sample. Eight ranges are used, spaced 100 milliseconds apart, starting at 400 milliseconds. The eight ranges thus used are shown in Table 3.

TABLE 2

| EVENT DESIGNATOR | |
|---|---|
| Event Type | Event Designator |
| AV | 0 (000) |
| AR | 1 (001) |
| PVE | 2 (010) |
| PV | 3 (011) |
| PR | 4 (100) |
| P@MTR-V | 5 (101) |

TABLE 2-continued

| EVENT DESIGNATOR | |
|---|---|
| Event Type | Event Designator |
| P@MTR-R | 6 (110) |

It is to be noted that the range divisions shown in Table 3 are only exemplary, as any desired number of ranges and divisions could be used.

TABLE 3

| Event Histogram Range Divisions | | |
|---|---|---|
| Range No. | Range, MSec | Range, PPM |
| 0 | <400 | >150 |
| 1 | 400-500 | 120-150 |
| 2 | 500-600 | 100-120 |
| 3 | 600-700 | 85.7-100 |
| 4 | 700-800 | 75-85.7 |
| 5 | 800-900 | 66.7-75 |
| 6 | 900-1000 | 60-66.7 |
| 7 | >1000 | <60 |

Each cycle time range has allocated thereto eight 3-byte bins, one for each event type. Each bin holds a counter that is incremented by the pacemaker whenever a given event type is detected for a given cycle time. The organization of the event histogram memory in range division, event types, and counter bins is graphically represented in FIG. 7.

Figure 7:
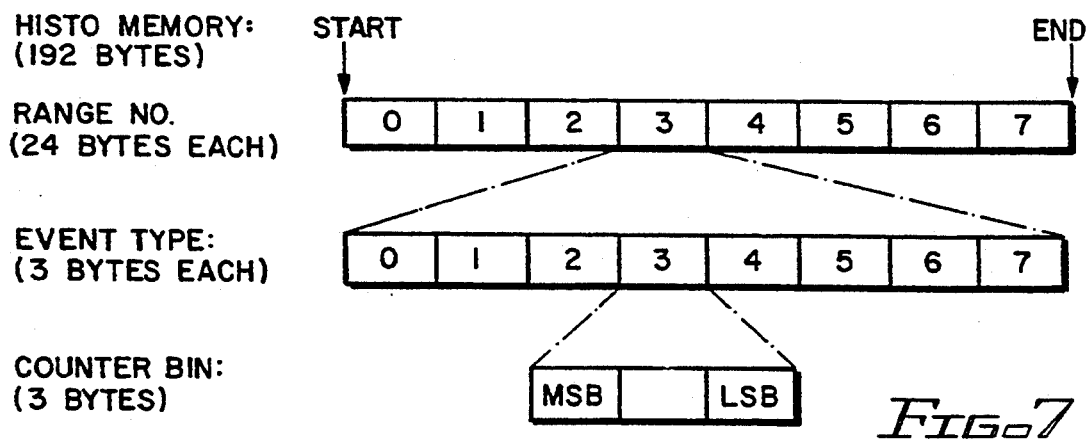
FIG. 7 shows the organization of an event histogram memory.

From FIG. 7, it is seen that the formula for calculating the absolute memory address of the MSB (most significant bit) of the bin to increment for any event/rate update is:

(START)+3×(Event Designator+(Range No.×8) where (START) is the Histogram starting address in the pacemaker memory 62.

It is noted that each 3-byte counter bin may contain a maximum value of 16,777,215. In operation, if any individual bin becomes filled to capacity, or "overflows," then counting in all bins stops until the Event Histogram data can be downloaded and cleared.

Figure 8:
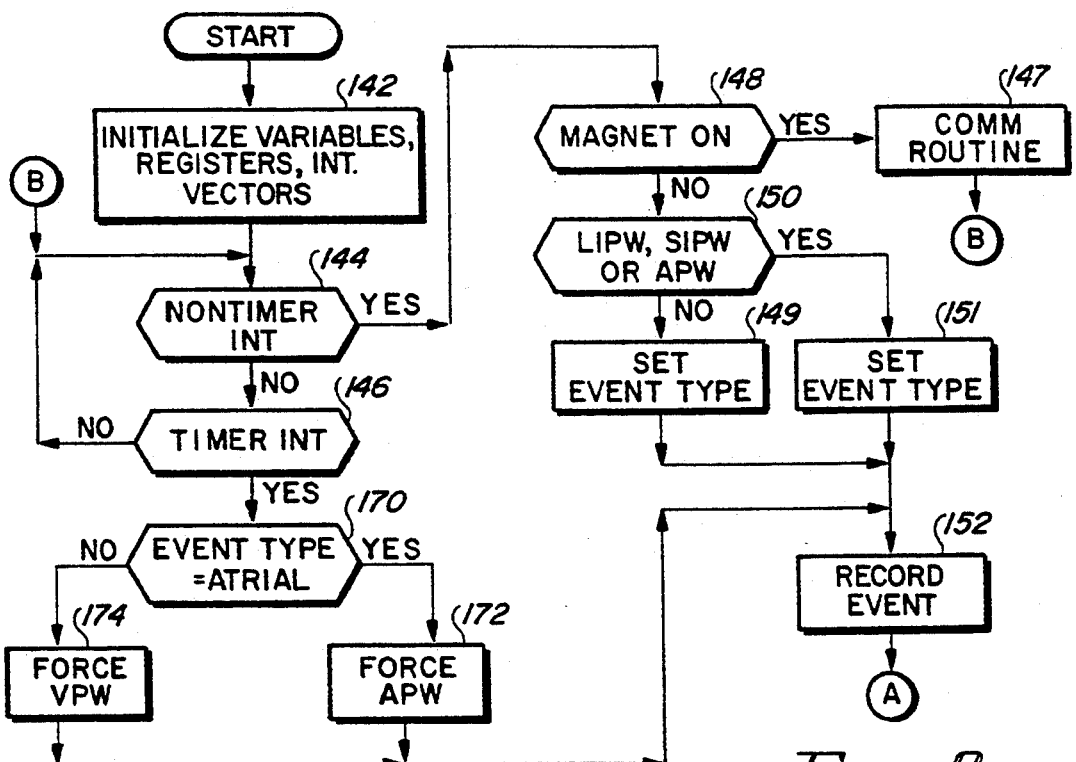
FIGS. 8, 9 and 10 are flowcharts illustrating the manner in which event histogram data is accumulated in the memory circuits of the implantable pacemaker in accordance with the present invention.
Figure 9:
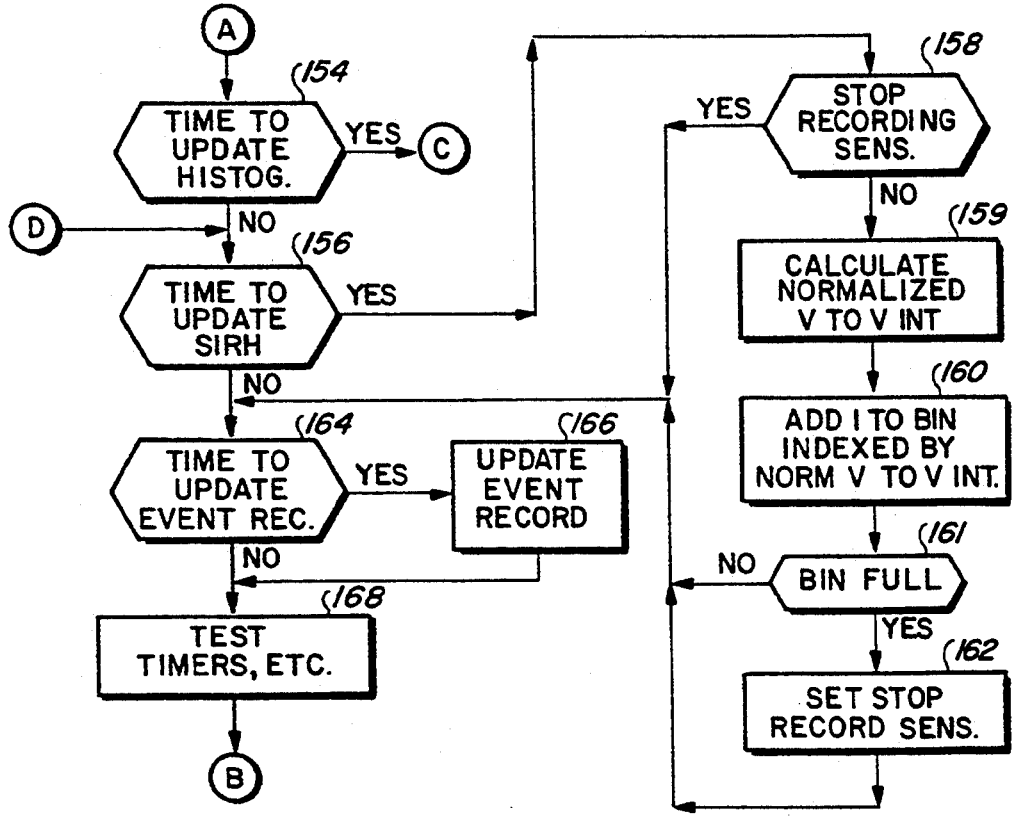

Referring next to FIG. 8, a flowchart is presented that illustrates the manner in which the pacemaker 16, and in particular the pacemaker state logic 42 and related processing circuitry, creates the event/rate data. As indicated above, in a preferred embodiment of the pacemaker 16, the pacemaker state logic 42 and the pacemaker timer circuits 50 may be realized using a suitable microprocessor 52. The flowchart shown in FIG. 8 thus represents the relevant portions of an operating program stored in memory 62 used to control the pacemaker 16 in accordance with the present invention. In FIG. 8, as in the other flowcharts used herein, each main program step is referred to as a "block," with a reference numeral being assigned to each block for identification purposes. As seen in FIG. 8, a first step of the process is to initialize the various variables, registers and interrupt vectors used by the microprocessor 52 (block 142). Note that an interrupt vector is simply an interrupt signal that acts as a trigger, causing a prescribed event to immediately take place. Once the initialization has occurred, a determination is made as to whether a non-timer interrupt is present (block 144). If not, then a next determination is made as to whether a timer interrupt is present (block 146). If not, then the program control loops back to block 144, and the process continues. In other words, the main branch of the program for the microprocessor 52 of the pacemaker 16, or equivalent state logic circuitry, is to wait for an interrupt signal to be received either from an non-timer source, or a timer source.

If an interrupt is received from a non-timer source, then a first step is to determine whether the magnet is on (block 148). The magnet is on only when the telemetry head 74 of the external programmer 20 is placed in position to establish the telemetry link 70 between the pacemaker 16 and the external programmer. Thus, if the magnet is not on, that means the external programmer is not present, and in such instance a determination is then made as to whether the non-timer interrupt signal is an LIPW, SIPW or APW (block 150). See Table 1 for a definition of these terms. If so, then that indicates the pacing events relate to the atrium, and an appropriate event type is defined (block 151). If not, then that indicates the pacing events relate to the ventricle (SIRH or VPW) and an appropriate event type is defined (block 149). The occurrence of such events is recorded (block 152) in a temporary buffer or latch register.

If the magnet is on (block 148), then that indicates the telemetry head of the external programmer is in place, and an appropriate communication routine is invoked (block 147) to establish the telemetry link 70 and to allow data to be transferred from the pacemaker, or to allow control parameters to be transferred to the pacemaker.

If an interrupt is received from a timer source (block 146), then a determination is made as to the type of interrupt (block 170). If the event is an atrial event, then an A-pulse is generated by forcing the APW state (block 172). Such APW event is recorded (block 152) in the temporary buffer register. If the event is not an atrial event, then a V-pulse is generated by forcing the VPW state (block 174). Such event is also recorded in the temporary buffer (latch) register (block 152). It is noted that the temporary buffer register functions as a latch circuit that keeps a temporary record of the last n events that have occurred, where n is at least two. This allows the most recent state changes of the pacemaker to be sampled when the sampling rate is not every event.

Figure 10:
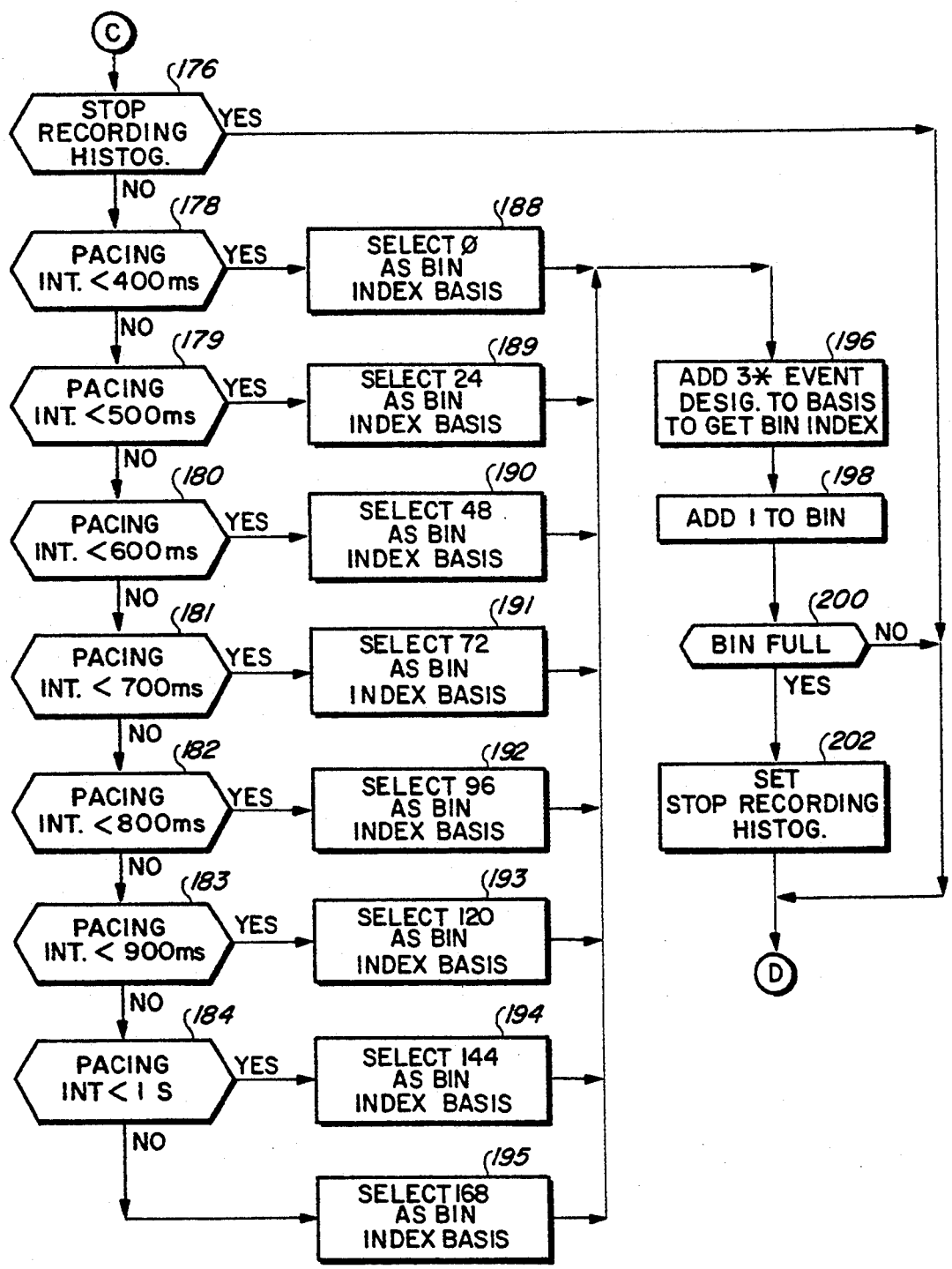

After recording the most recent state changes (block 152), the appropriate timers are checked to determine if it is time to update the event histogram (block 154). The event histogram is updated at the sample time. The sample time is a programmable parameter, and may be either every event, every 1.6 seconds, or every 26 seconds. If it is not time to update the event histogram, or after updating the event histogram, a next determination involves whether it is time to update the sensor-indicated rate histogram (SIRH) (block 156). The SIRH histogram is a histogram that keeps track of the sensor-indicated rate as derived from the physiological sensor 26. If it is time to update the SIRH, then the SIRH is updated as depicted in blocks 158–162. Note that the SIRH is not part of the present invention, and will not be described herein. A description of the SIRH may be found in the '052 patent, cited above. See particularly FIG. 10 of the '052 patent and accompanying text.

Next, a determination is made as to whether it is time to update the event record (block 164). If so, then the event record is updated (block 166). After such updating, or if not time to update, then the various timers used within the timer block 50 are tested (block 168), and other housekeeping tasks are performed, prior to going back to the main wait loop (beginning at block 144). It is noted that the event record is also not part of the present invention, but is considered as a separate invention that is described in commonly owned and copending patent application Ser. No. 07/846,460, entitled METHOD AND SYSTEM FOR RECORDING AND REPORTING A SEQUENTIAL SERIES OF PACING EVENTS, filed concurrently herewith, which patent application is incorporated herein by reference. Other copending and commonly owned patent applications that are incorporated herein by reference include Ser. No. 07/844,818, entitled METHOD AND SYSTEM FOR AUTOMATICALLY ADJUSTING THE SENSOR PARAMETERS OF A RATE-RESPONSIVE PACEMAKER, filed concurrently herewith; and Ser. No. 07/844,807, entitled RATE-RESPONSIVE PACEMAKER HAVING SENSOR THRESHOLD WITH OFFSET, filed concurrently herewith.

The manner in which the event histogram is updated is depicted beginning at block 176. A first step of such updating involves determining if the histogram is full (block 176) as indicated by a bin-full flag. If so, then no further changes are allowed to take place in the event histogram data (i.e., the event histogram is "frozen") until the bin-full flag is reset and the event histogram is cleared (which occurs during initialization, block 142). If the histogram is not full, then a determination is made as to the rate range. Such determination is made by examining the pacing interval to determine its duration (blocks 178–184). The rate ranges are as described above in Table 3. Depending upon the rate range determination, a corresponding index basis is assigned (blocks 188–195). Next, the specific address of the cell within the event histogram where the pacing event is to be stored is calculated (block 196). Note that this determination is based on the event designator for the particular pacing event that has most recently occurred at the sample time. The event designators are shown above in Table 2. The most recently occurred pacing events are determined by examining the contents of the temporary buffer register(s) as recorded at block 152.

In order to preserve the integrity of the data stored in the event histogram 140, an event histogram change (EVHSTCHG) bit is used within the memory 62 at a specified address. Such EVHSTCHG bit is set and cleared entirely under programmer control, i.e., it is neither read nor written by the pacemaker itself. It is used to provide a histogram validation function. On the first occasion in any given programming session that a permanent parameter is programmed for the current pacemaker, the EVHSTCHG bit is set. Subsequently, the EVHSTCHG bit is examined upon an operator request for a display of the Event Histogram data. If it is found to be set, and if there is no current request to clear the Event Histogram, a warning message is displayed to indicate that the current Event Histogram data may no longer be valid, because of a change in a possible relevant parameter. The EVHSTCHG bit is cleared by the programmer whenever the Event Histogram data is cleared.

The Event Histogram data is also cleared automatically by the pacemaker itself upon a mode change of the pacemaker. A pacemaker mode change is normally initiated from the external programmer 20. Whenever such mode change is made, the operator is prompted to confirm the operation, since the Event Histogram data is cleared upon making such a mode change. By "mode" it is meant the mode of operation, such as SENSOR OFF, SENSOR PASSIVE, SENSOR ON, and whether the pacemaker is to be configured to operate as a single- or dual-chamber pacemaker. A three or four letter code is frequently used to designate the pacemaker mode, as is known in the art. For example, the mode DDDR indicates the pacemaker is operating in a DDD mode (pacing and sensing in both heart chambers) with the physiological sensor being programmed to be ON.

Event Histogram data may also be cleared in the extremely unlikely event that a hardware, software, or data transmission error is detected internally by the pacemaker. In this situation, various responses occur, depending upon the particular model of pacemaker that is used. For example, if the pacemaker is a Synchrony II pacemaker, such internal error detection causes the SENSOR OFF mode to be assumed, and all rate-responsive functionality of the pacemaker is suspended until the magnetic reed switch is detected as closed (meaning that the telemetry head 74 has been placed in position).

Processing/Displaying the Event Histogram Data

With the event histogram data stored in the memory 62 of the pacemaker 16, it remains to download such data so that it can be processed and displayed. Such downloading is accomplished through the telemetry link 70 established by the external programmer 20. Advantageously, by using the APS-II/MTM processing circuits and memory as controlled by an appropriate processing program stored in the program cartridge 86, such data can be displayed in various graphical formats. Further, statistical data associated with the event histogram data can be computed.

Figure 13:
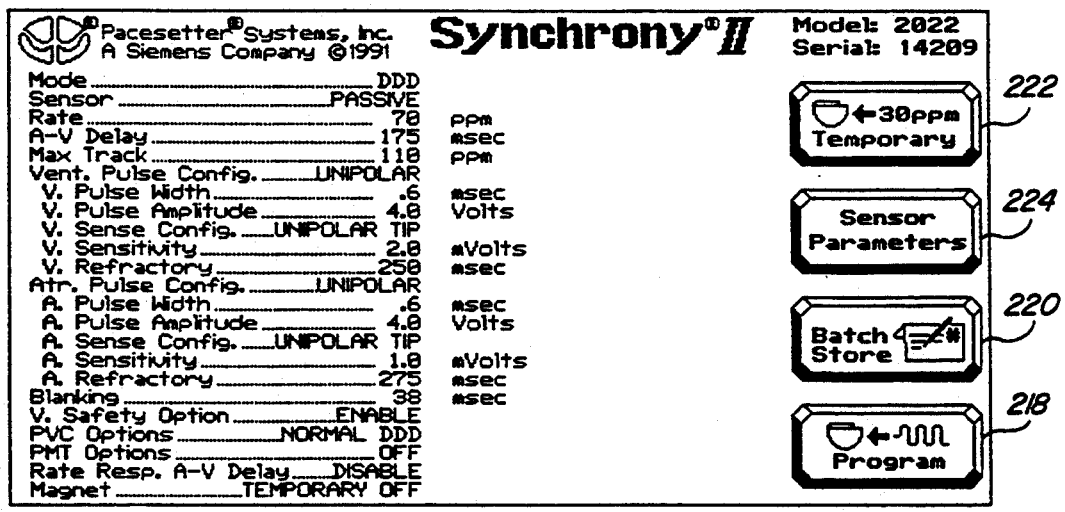
FIG. 13 illustrates a typical set of dual-chamber parameters that are programmed into the implantable pacemaker of FIG. 5 as displayed on a display screen of the external programmer.

To illustrate the usefulness of the event histogram data, reference is next made to FIG. 13 where there is shown the type of information that may be derived from the event histogram data of FIG. 6. FIG. 13 shows a stacked histogram 208 of the data presented in FIG. 6. That is, using a shading key 210 as shown in FIG. 6, a graphical representation that depicts the number of particular pacing events that occur at specific rates can be generated Note, that in FIG. 13 a vertical bar is used to depict the number of events of a particular type that occurred, with the vertical bar being sectionalized (using the shading key 210) to indicate the rate range of the events that make up the total number of events that occurred. Thus, as seen in FIG. 6, the largest number of pacing events that occurred were the PR events in the 76-85 ppm range (some 4,169,512 events were logged). Thus, in the graphical stacked histogram shown in FIG. 13, the largest section of the vertical bar corresponding to PR events is a section 212. By comparing t he height of the bar section 212 to the numerical axis of the stacked histogram 208, it is seen that it is approximately 4,200,000 counts high. In a similar manner, all of the other pacing event and their respective rates as indicated in the event/rate histogram data shown in FIG. 6 can be included in the stacked histogram 208 shown in FIG. 13.

In addition to the graphical information shown in FIG. 13, statistical information is also computed. For example, the following information may be computed from the data shown in FIG. 6:

Percent Paced in Atrium 26%
Percent Paced in Ventricle 47%
Total Time at Max Track Rate—0 Days, 0 Hrs, 0 Minutes, 3 Seconds.
Total Time Sampled—184 Days, 16 Hrs, 3 Minutes, 55 Seconds.

In computing statistical information such as that shown above, the "percent paced" may refer to either the "percent of time" or the "percent of events." The numbers shown above are the "percent of events." Thus, the "Percent Paced in Atrium" above is calculated by the sum of the AV and AR events divided by the total event count. Similarly, the "Percent Paced in Ventricle" is the sum of the AV and PV events divided by the total count. If the "percent of time" were displayed instead, then the message would read "Percent of Time Paced in Atrium" (or equivalent language), and the number displayed would be based on the time of the atrial events divided by the total time over which the data was collected.

The "Total Time at Max Track Rate" is determined by the product of the average interval times the event count summed for each rate bin associated with the P@MTR-V event types.

If every event is sampled, the "Total Time Sampled" is found by multiplying the number of events for each rate bin by the average interval for that bin, and accumulating the sum until all rate bins are included. In other words, the total time is equal to the sum of the reciprocal of rate for each pacing event. If the 1.6 or 26 second sampling rate is used, the "Total Time Sampled" is simply the product of the total count and the sampling rate.

Figure 12:
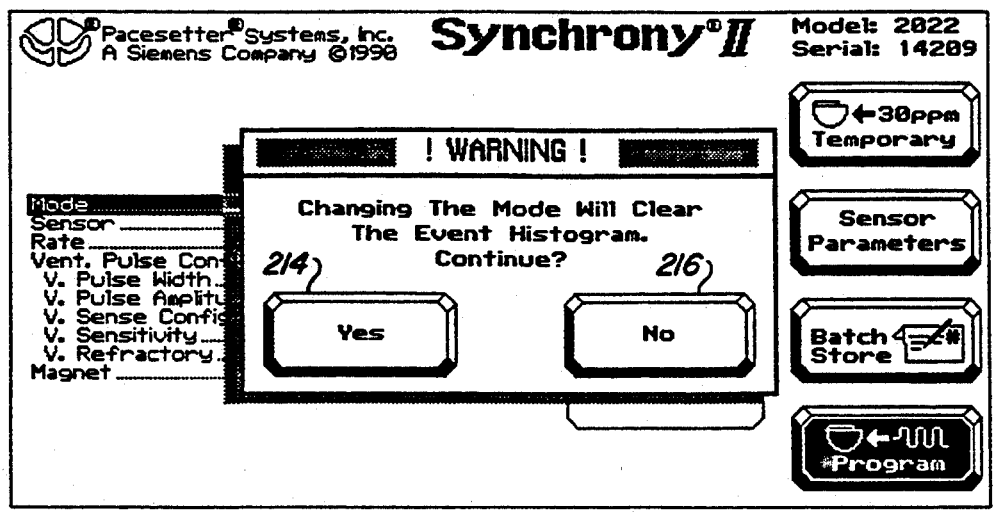
FIG. 12 illustrates a typical instructional screen displayed by the external programmer whenever the pacemaker mode is changed, which screen emphasizes that the event histogram data will be cleared upon a mode change.

Turning next to FIG. 12, a typical instructional screen displayed by the APS-II/MTM display 80 is depicted. The particular screen shown in FIG. 12 is displayed whenever the pacemaker mode is changed. The screen emphasizes that the event histogram data will be cleared upon a mode change.

The screen shown in FIG. 12, as well as the other screens shown in the other figures, is displayed using the CRT 92 of the APS-II/MTM. The touch screen 78 overlays the screen, so that all the operator need do is touch the area 214, for example, to continue with the mode change. Should the operator choose not to proceed with the mode change, then all he or she would need to do is to touch the area 216 of the screen. Note that the event histogram is cleared upon making a mode change in order to insure that such data is meaningful. Counting pacing events and determining their respective rates with multiple modes could produce meaningless and misleading information.

FIG. 13 illustrates a typical set of dual-chamber pacing parameters as programmed into the implantable pacemaker 16 of FIG. 5 as displayed on a display screen of the APS-II/MTM programmer 20. Such parameters define the behavior of the pacemaker state machine 42. Note that there are four "buttons" or icons displayed along the right edge of the display shown in FIG. 13. Touching the "Program" icon 218, for example, causes the information displayed on the screen to be programmed into the memory 62 of the pacemaker 16. Touching the icons 220 or 222 ("Batch Store" or "30 ppm Temporary" cause various diagnostic and data features not relevant to the present invention to be invoked. Touching the icon 224, "Sensor Parameters" causes the sensor parameter screen shown in FIG. 14 to be displayed.

Figure 14:
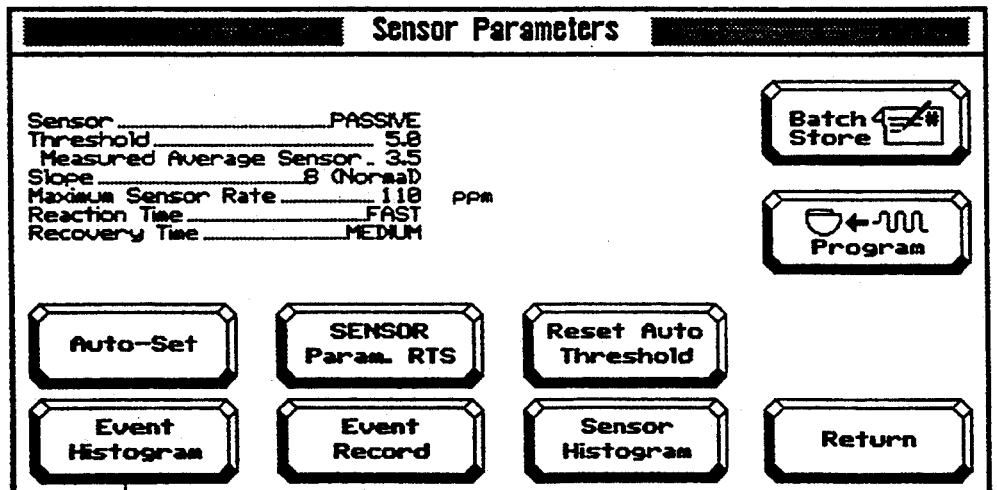
FIG. 14 illustrates a typical set of sensor parameters that are programmed into the implantable pacemaker of FIG. 5 as displayed on a display screen of the external programmer.

The Sensor Parameter screen shown in FIG. 14 illustrates a typical set of sensor parameters that are programmed into the implantable pacemaker 16. Note that the sensor parameters are a subset of the Pacemaker Parameters, which parameters define the behavior of the Rate-Responsive Sensor Processor, which is a subsystem of the Pacemaker State Machine 42. Of particular relevance to the present invention is the icon 226 in the lower left-hand corner of the sensor parameter screen of FIG. 14. By pressing or touching the icon 226, the Event Histogram features of the invention are accessed.

Figure 15:
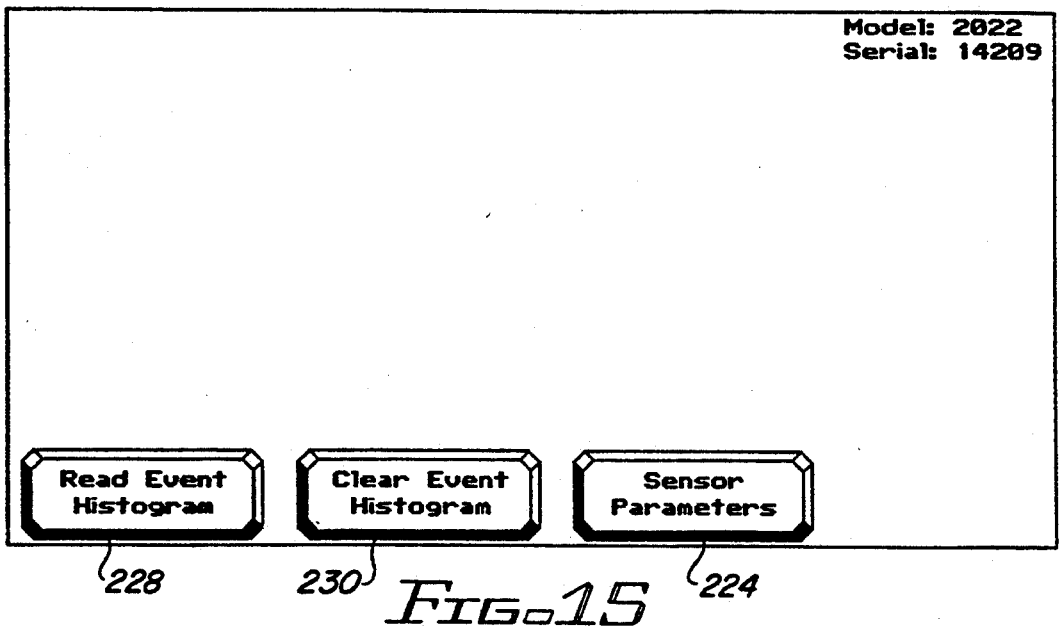
FIG. 15 illustrates the initial event histogram screen that is displayed on the display screen of the external programmer whenever the "Event Histogram" option included in the display of FIG. 14 is selected.

When the icon 226 is first touched, the initial Event Histogram screen is displayed as shown in FIG. 15. This screen illustrates how the user is prompted to indicate whether the histogram is to be READ, by touching the "Read Event Histogram" icon 228, or cleared, by touching the "Clear Event Histogram" icon 230. Touching the "Sensor Parameters" icon 224 causes the Sensor Parameter Screen shown in FIG. 14 to again be displayed.

Figure 16:
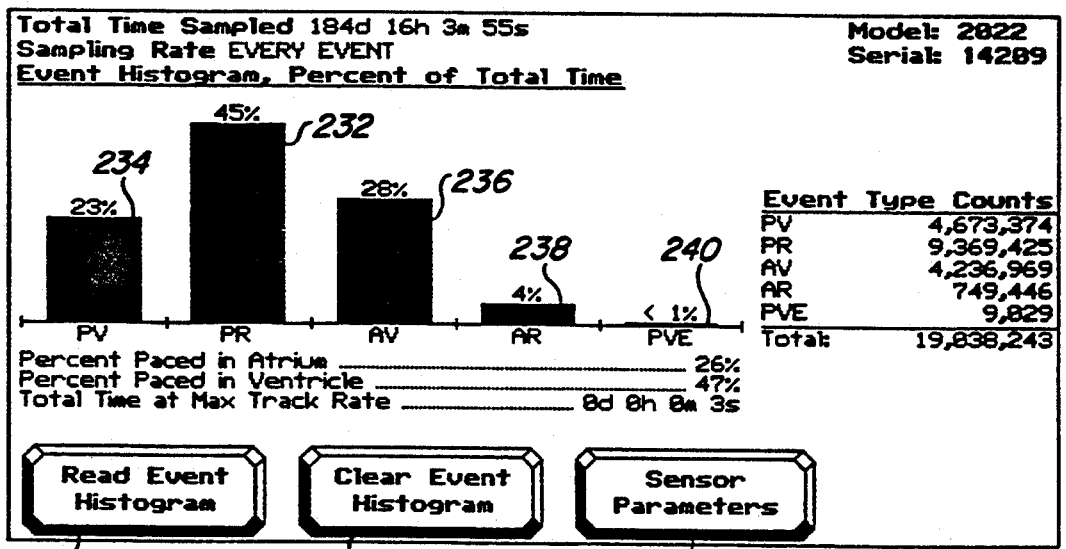
FIG. 16 depicts a typical Event Histogram screen display as generated by the external programmer in accordance with the present invention.

If the "Read Event Histogram" icon 228 of FIG. 15 is touched, the event/rate histogram data downloaded from the pacemaker is processed and displayed as shown in FIG. 16. Note that the display indicates at the top left portion of the screen the Total Time Sampled (which in the example shown is 184 days, 16 hours, 3 minutes and 55 seconds). Also indicated is the sampling rate (every event). The Event Histogram is then shown, with five events illustrated: PV events, PR events, AV events, AR events, and PVE events. Each event is graphically illustrated as a vertical bar, with the relative height of the bar being indicative of the percent that the event occurred. As shown in FIG. 16, the percent shown is the percent of the total time (as opposed to a percent of the total events). Thus, the PR events (which, for purposes of the display shown in FIG. 16 include P@MTR-R events) are depicted as a bar 232 having the greatest height, corresponding to events that occurred 45% of the time. The percent is indicated as a number at the top of the bar. The PV events (which, for purposes of the display shown in FIG. 16 include P@MTR-V events) are depicted as a bar 234 having a height about ½ that of the PR bar 232, corresponding to events that occurred 23% of the time. The AV events are depicted as a bar 236 having a height that is also about ½ that of the PR event bar 232, corresponding to events that occurred 28% of the time. The AR events are likewise depicted as a bar 238 having a very short height, corresponding to events that occurred only 4% of the time. The PVE events are also depicted as a bar 240. However, the PVE events for the example shown only occurred less than 1% of the time, so the relative height of the bar 240 appears as a straight line.

Below and to the side of the histogram bars displayed on the screen of FIG. 16 are selected statistics relating to the event histogram data. The event type counts are displayed to the side. These events correspond to the total counts for each event type for all of the rate ranges shown in FIG. 6. The total event type counts is also computed and displayed.

The Percent Paced in the Atrium is computed from the event type counts to be 26%. The Percent Paced in the Ventricle is similarly computed to be 47%. Note that these percents, unlike the percents indicated at the top of each histogram bar, are based on the percent of events. The total time at the Max Track Rate is also displayed, which for the example shown is 0 days, 0 hours, 0 minutes, and 3 seconds.

FIG. 17 shows a popup screen 242 that is used by the APS-II/MTM programmer to clear an Event Histogram, such as the Event Histogram shown in FIG. 16, and to thus clear the event counter data maintained within the memory 62 of the pacemaker 16. The popup screen 242 shown in FIG. 17 appears whenever the "Clear Event Histogram" icon 230 is touched. This popup screen also illustrates how the user is prompted to change the sampling rate. That is, a thumbwheel switch icon 244 appears on the left side of the popup screen 242. The user simply touches the sampling rate that is desired, and that sampling rate will be used for the next batch of event and rate data gathered for the Event Histogram. Also, the user must confirm, by touching the "OK" icon 246, that the Event Histogram is to be cleared. If the Event Histogram is cleared, the display appears as shown in FIG. 18.

Generally, a user will print the Event Histogram prior to clearing it, so that a hard copy record is maintained of the Event Histogram data. Printing is achieved by touching an appropriate one of the permanent "buttons" 243 located below the CRT display 92 on the APS-II/MTM device (see FIG. 4). The printed report contains additional information not available on the programmer screen due to the abbreviated space available on the programmer screen. An example of the type of report that is printed out from the APS-II/MTM is shown in FIG. 19. The information contained within the printout shown in FIG. 19 includes the same information that is contained within the Event Histogram Table of FIG. 6, as well as the graphical representations and statistical information generated for the screen shown in FIG. 16. Included in the printout shown in FIG. 19 is a summary of the pacemaker operating parameters that existed at the time the Event Histogram was interrogated. Such operating parameters include the pacemaker mode (which is the DDDR mode for the example shown); the sensor status (ON, OFF, or PASSIVE); the programmed rate (e.g., 70 ppm); the Max Track Rate (e.g., 110 ppm); the Max Sensor Rate (e.g., 110 ppm); the A-V Delay (e.g., 175 msec); and the Rate-responsive A-V Delay (ENABLE or DISABLE).

It is noted that when the Event Histogram is displayed, such as is shown in FIG. 16, that the Histogram data does not change as the pacing event data continues to be recorded within the pacemaker. This is because the event data is communicated from the pacemaker in blocks; not in real time. Hence, that which is displayed on the APS-II/MTM screen as shown in FIG. 16 is only a "snap-shot" of the data as it existed at the time the data was transferred from the pacemaker through the telemetry link. However, it should be noted that if another type of communication protocol were implemented, which could, in effect, transmit data from the pacemaker in real time, then the Event Histogram displayed could be interactive with the actual data sensed, thus allowing the Event Histogram and associated statistics to always contain the latest pacing event information.

Figure 18:
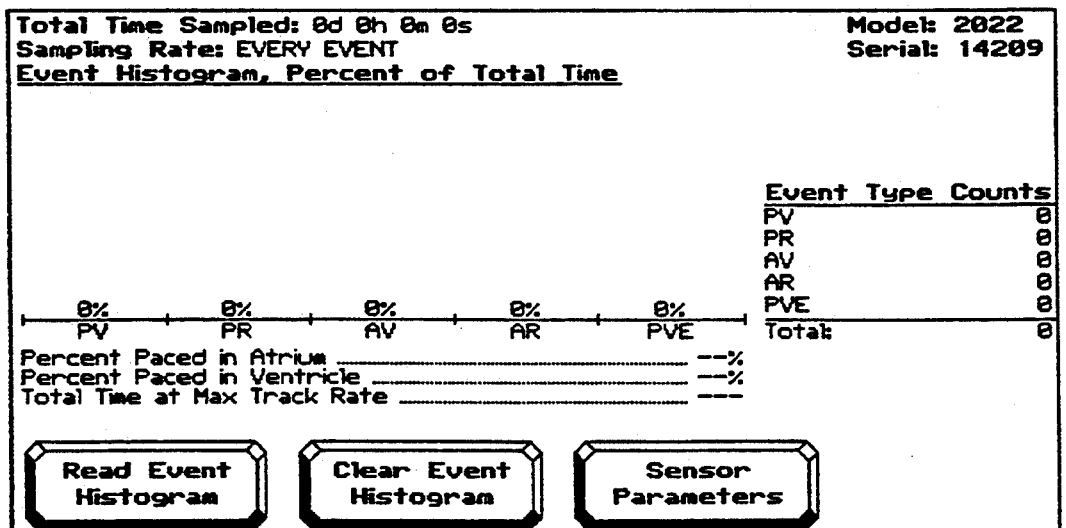
FIG. 18 shows the Event Histogram screen display as generated by the external programmer immediately after clearing the event histogram.

Referring next to FIG. 18, a flowchart is shown that illustrates the manner in which the APS-II/MTM programmer processes the event histogram data downloaded from the implantable pacemaker in order to generate and display an event histogram and related statistics.

Figure 20:
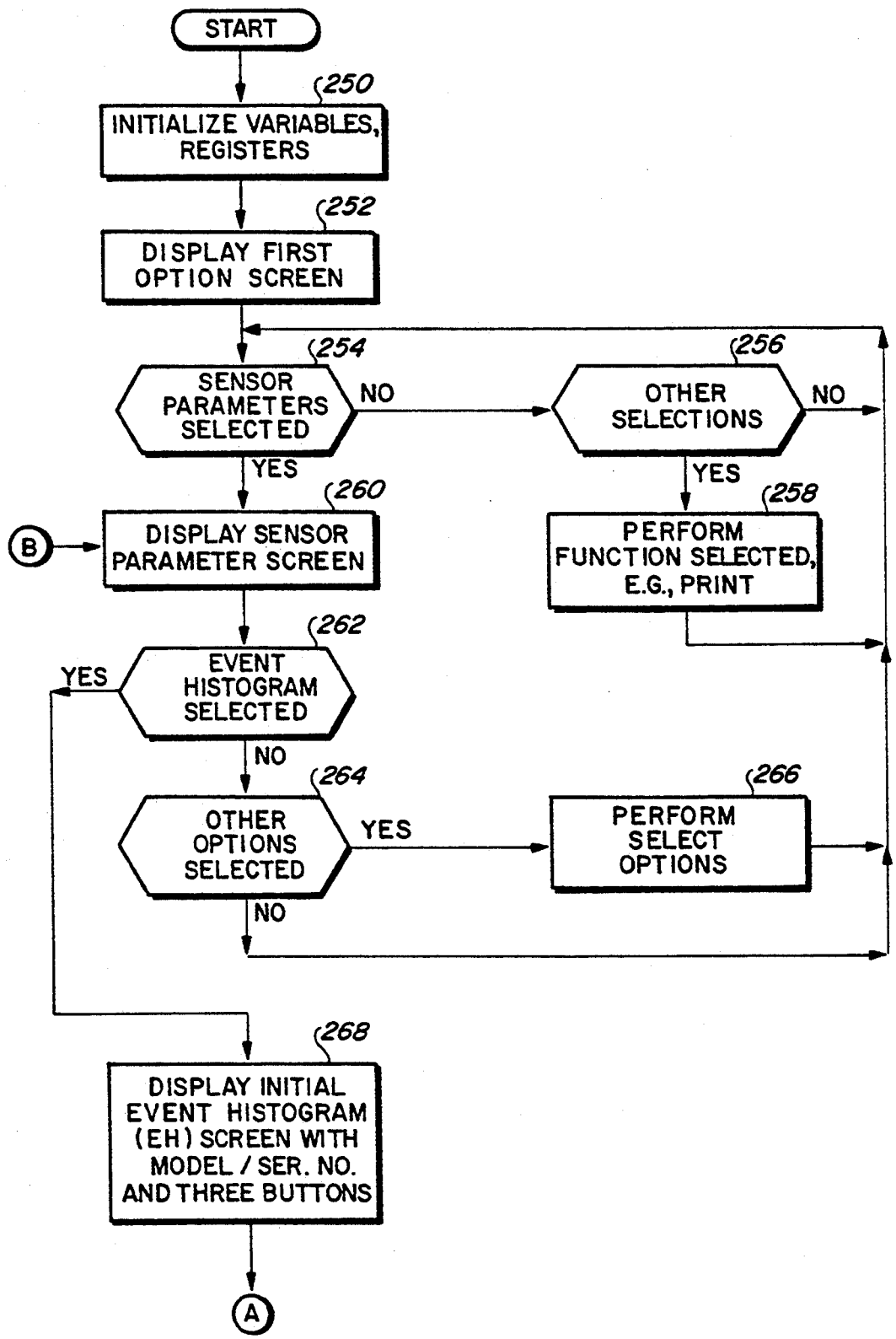
FIGS. 20 and 21 are flowcharts illustrating the manner in the external programmer processes data downloaded from the implantable pacemaker in order to generate and display an event histogram.
Figure 21:
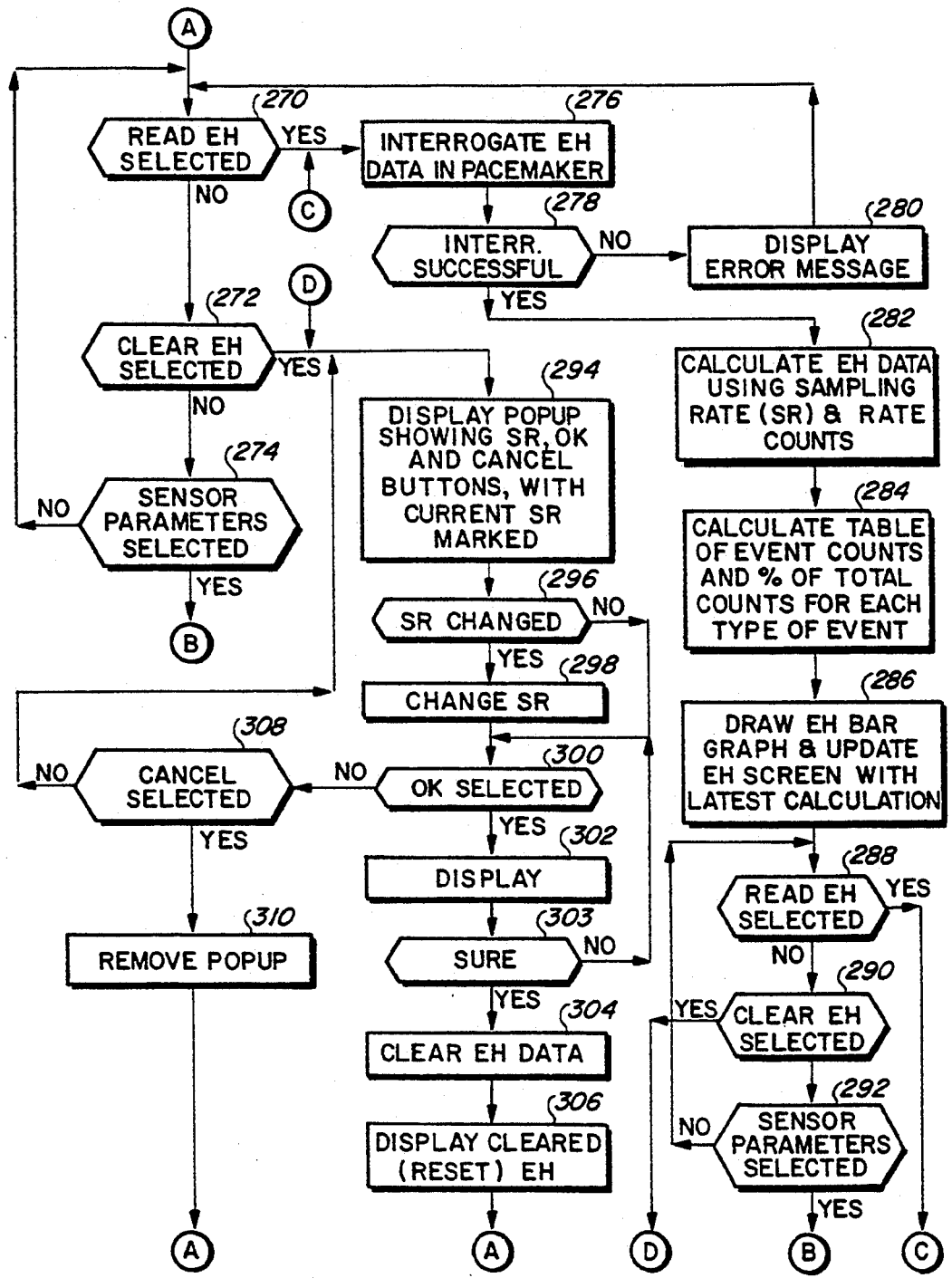

As seen in FIG. 18, starting with FIG. 20, a first step of the process is an initialization step (block 250), which actually involves several steps, and may involve the display of several preliminary screens on the APS-II/MTM display screen 80. During initialization, appropriate variables and parameters are set, various housekeeping functions are performed, and appropriate instructions are given to the user to establish the telemetry link with the pacemaker. Once the initialization steps are complete, a first option screen is displayed (block 252). This first option screen allows the user to select one of several displayed options. One of the options is "Sensor Parameters." If the "Sensor Parameters" option is selected (block 254), which selection is made by simply touching the area of the APS-II/MTM display screen whereon the Sensor Parameter icon is displayed (which icon has the appearance of a "push button"), then the Sensor Parameter screen is displayed (block 260). The sensor parameter screen is as shown in FIG. 14. If the Sensor Parameter option is not selected (block 254), and if other options are likewise not selected (block 256), then nothing happens, and the APS-II/MTM simply waits until it receives some operator command. If another option is selected (block 256), then that particular option is performed (block 258). Note that one of the options that may be performed is to print the information displayed on the APS-II/MTM screen. In some instances, including the printing of the Event Histogram in accordance with the present invention, the information printed is more comprehensive than the information displayed because of the space limitations on the display screen.

As seen in FIG. 14, the Sensor Parameter screen contains several options that may be selected. For purposes of the present invention, one of these options is "Event Histogram." If the Event Histogram option is not selected (block 262), but another option is selected (block 264), such as "Sensor Histogram" or "Event Record," then such other selected option is performed (block 266). As always, if no other selections are made, the APS-II/MTM waits until an appropriate selection is made.

Still referring to FIG. 18, when "Event Histogram" is selected (block 262), the initial Event Histogram screen is displayed (block 268). The initial Event Histogram screen is as shown in FIG. 15, and includes a display of the model and serial number of the pacemaker with which the telemetry link has been established, and also displays three icon buttons.

A first of the three icon buttons displayed is a "Read Event Histogram" button. (Note in FIG. 18 that Event Histogram is abbreviated as "EH.") A second is the "Clear Event Histogram" button. A third is the "Sensor Parameters" button. A determination is made by the APS-II/MTM processing program as to which of these three buttons is selected (blocks 270, 272 and 274). If none is selected, then the program waits until one is selected, unless another type of overriding selection (interrupt) occurs. If the "Sensor Parameter" button is selected (block 274), then the APS-II/MTM program causes the sensor parameter screen (FIG. 14) to be redisplayed. If the "Read Event Histogram" button is selected (block 270), then the Event Histogram data stored in the pacemaker is interrogated (block 276). If the interrogation is successful (block 278), i.e., if the event/rate data is successfully downloaded, then the data needed for the Event Histogram display (which includes both a table, as shown in FIG. 6, and a bargraph, as shown in FIG. 16), as well as the statistics associated with such data, is calculated (blocks 282, 284). Then, the Event Histogram bargraph, as shown in FIG. 16, is drawn on the APS-II/MTM screen (block 286), and updated with the latest statistical calculations.

Once the Event Histogram has been displayed, it may be updated by again selecting the "Read Event Histogram" button (block 288), which is included at the bottom of the Event Histogram screen along with the "Clear Event Histogram" and "Sensor Parameters" buttons. If the "Read Event Histogram" button is selected, then the program repeats the interrogation of the Event Histogram data in the pacemaker (block 276), new calculations are made (blocks 282, 284) and an updated screen is displayed (block 286). If the "Sensor Parameters" button is selected (block 292), then the Event Histogram (FIG. 16) is replaced with the Sensor Parameter screen (FNNIG. 12).

Still referring to FIG. 18, if the "Clear Event Histogram" button is selected (block 272 or 290), then a popup screen is displayed over the top of the current screen that shows three buttons. A representation of the popup screen is shown in FIG. 17. One button of the popup screen is a "Sampling Rate" button, and allows one of three sampling rates to be selected (Every Event, 1.6 seconds, or 26 seconds). One button is an "OK" button which confirms that the Event Histogram is to be cleared. The other button is a "Cancel" button, which is selected if the user does not wish to clear the Event Histogram.

Once the popup screen is displayed, a determination is made as to the selected sampling rate. The current sampling rate is highlighted. If a new sampling rate is desired for the next event histogram, then the user simply touches the desired rate, and the new rate is highlighted. If the sampling rate is changed (block 296), then the appropriate pacemaker parameter controlling sampling rate is set for reprogramming in the pacemaker (block 298).

Even though the sampling rate is set to a desired value for the next Event Histogram, the sampling rate will not be changed until the current Event Histogram is cleared. To clear the Event Histogram requires that the "OK" confirmation button be depressed. If depressed (block 300), then an appropriate warning may be displayed reminding the user that the current histogram data will be lost and cannot be printed if cleared (block 302). Hence, before clearing the Event Histogram data, most users will print such data. After confirming that the Event Histogram is to be cleared (block 303), the Event Histogram is cleared (block 304), and the display of the Event Histogram is likewise cleared (block 306). An example of a cleared Event Histogram display is shown in FIG. 18.

If the "Cancel" button is selected at the popup screen display (block 308), then the popup screen is removed (block 310), revealing the prior screen. If the "Cancel" button is not selected, and if neither the "OK" nor "Sampling Rate" buttons are selected, then the APS-II/MTM program just waits for a selection to occur, or for an interrupt to occur.

Overview and Summary of the Pacing System

As seen from the above description, the pacemaker has reserved 168 bytes of storage space for the event/rate counters. This storage is organized into eight rate ranges, each of which has seven event types, each of which has a three-byte (24-bit) count field. Thus, $8 \times 7 \times 3 = 168$ bytes are used, and the maximum count for any given bin is $2^{24} - 1 = 16,777,215$.

The logic incorporated into the pacemaker tracks the pacemaker state machine. When an event occurs, the logic determines the event type. If the sampling rate is "every event," the appropriate counter is incremented, based on the rate and event type. If the 1.6 second or 26 second sampling rate is programmed, the event is latched so that when the sampling interval timer expires, the appropriate counter can be incremented.

The data is accumulated by the pacemaker continuously. Data is not cleared unless the pacing mode is changed, the sensor mode is set to OFF, a clear command is requested by the user, or the pacemaker goes through an error recovery sequence. Data is frozen if any counter reaches its maximum count.

The programmed parameters of the pacemaker influence the event types and rates recorded. The interaction between the timers, the maximum intervals, and the intrinsic activity of the patient's heart ultimately determines the results.

The event counter data is accessible at any time by an external programmer through the use of a telemetry link. The pacemaker contains communication algorithms which modulate the telemetry channel to transmit the Event Counter data.

The programmer extracts the event counter data from six blocks of 32 bytes each. The data is then decoded to produce a table of event types versus rate. Calculations are performed to compute the sum of counts for each event type and the total event count. The total time sampled, the percent of counts paced in the atrium and ventricle, and total time at the Max Track Rate are also calculated.

To present the data to the user, the tables are displayed and/or printed by the programmer. In addition to showing the data in tabular form, histograms are produced which show the percentage of total time the pacemaker was functioning in each event type. Above each histogram bar the percentage is given in numeric form.

The user may also request that the event counter data be read and reformatted, or may clear the data. A confirmation of the latter action is required to ensure that data is not inadvertently lost. In addition, the sampling rate is selected part of the clearing process.

Access to the parameters controlling the rate-responsiveness of the pacemaker is provided. The accumulated event counter data is not affected by changing any parameters, except for Sensor and Mode. Future data may be affected due to the influence of the rate-responsive algorithm of the pacemaker's microprocessor program.

The printed report contains additional information not available on the programmer screen, such as selected parameters and the complete rate versus event type table. The screen presentation is abbreviated due to the available space.

Using the Invention to Set Programmed Parameters

Advantageously, the present invention may be used to provide a method of optimally setting the programmable parameters of a programmable implantable pacemaker implanted within a particular patient. The implantable pacemaker is as described above, i.e., it includes means for counting and storing the number of state changes of the pacemaker and the frequency of occurrence (rate) of such state changes. The method includes the following steps:

1. The patient is subjected to a known level of activity in accordance with a prescribed exercise regime.

2. The number of state changes of the pacemaker and the rate of occurrence of such state changes is recorded within the pacemaker memory circuits during the prescribed exercise regime.

3. A data link is established between the implantable pacemaker and an external programmer device and the information recorded in step 2 above is downloaded to an external programmer device through the established data link.

4. The information downloaded in step 3 is examined to determine if a prescribed number of state changes occurred within specified rate ranges commensurate with the prescribed exercise regime followed in step 1.

5. The programmable parameters of the implantable pacemaker are adjusted through the established data link using the programmer device in order to make the pacemaker optimally responsive to future patient activity. An optimally responsive pacemaker is considered as one which undergoes a reasonable number of state changes of a prescribed type and rate given the level of activity undertaken by the patient in the prescribed exercise regime.

Advantageously, steps 1 and 2 of the method described above may be carried out by the patient prior to visiting the medical personnel who will program (optimally set the operating parameters of) the pacemaker. That is, the patient may be instructed when setting up the appointment with the medical personnel to undertake the prescribed exercise regime one or two hours before arriving at the medical clinic or office where the programming is to be done. When the patient arrives, the pacing event data is downloaded from the pacemaker and analyzed by the medical personnel based on the exercise regime followed by the patient. When the information is downloaded, it may be presented as an Event/Rate Histogram, as described above. From this information, and other information known to the physician, the medical personnel can ascertain if the operating parameters of the pacemaker have been optimally set.

AN EXAMPLE

As a practical example that illustrates the utility of the Event Histogram capability of the present invention, the following discussion is provided:

Chronotropic incompetence is usually defined as the failure to increase the heart rate above 100 bpm (beats per minute) in response to a maximal physiologic stress. However, this definition may be too limited, as there are other factors that should be considered in addition to the heart rate, such as the patient's age, underlying disease processes and the actual activity performed. While failure to achieve a heart rate of 100 bpm might well be chronotropic incompetence, the failure to achieve a heart rate of 130 or even 150 ppm if the individual were 20 years old and not on any medications that might blunt sinus node responsiveness may also be chronotropic incompetence. Further, while only 10 to 20 percent of patients will have symptoms indicative of chronotropic incompetence with their primary indication for cardiac pacing, an additional 30 percent or more may develop chronotropic incompetence over time due to the progression of their intrinsic disease process or a related complication of their medical therapy.

Before implantation of a pacemaker, the assessment of chronotropic incompetence is relatively "simple." One need only obtain an exercise tolerance test evaluating the patient for the peak sinus rate achieved. While simple, such test may not always be practical depending upon the patient's presenting symptoms and concomitant medical conditions. Further, an exercise test is relatively expensive.

Advantageously, a programmable pacemaker having the Event/Rate Histogram capability as described herein may be implanted that greatly facilitates the ability to assess the presence of chronotropic incompetence. The pacemaker, when initially implanted, has its sensor programmed to PASSIVE. This means that the sensor has no effect on the determination of the pacing rate, but the sensor-indicated rate, as well as the actual rate are indicated and stored in the Event/Rate Histogram and SIRH. (For some patients, it may be desirable to program the sensor to OFF in order to increase longevity by reducing the battery current drain. For such patients, the sensor may be programmed to PASSIVE on an annual basis for a period of two to four weeks. Such is readily accomplished by having the patient come to the medical office approximately one month prior to the scheduled evaluation. Once the system is interrogated, the sensor is programmed from OFF to PASSIVE.) When the patient comes to the medical office for the routine follow-up visit, the Event/Rate Histogram feature is interrogated. The Event/Rate Histogram data will clearly indicate whether chronotropic incompetence is identified. If it is, the rate-responsive features of the pacemaker may to activated in order to provide appropriate therapy.

In addition to facilitating the diagnosis of chronotropic incompetence, there are numerous other occasions where the Event/Rate Histogram information provided by the present invention is extremely useful to a physician. For example, the physician may want to intentionally place a limit on the patient's intrinsic heart rate. Alternatively, the physician may have a physiologic sensor that is too sensitive for a given patient, or overly insensitive for a given patient. See, e.g., Levine, P. A., "Utility and Clinical Benefits of Extensive Event Counter Telemetry in the Follow-Up and Management of the Rate-Modulated Pacemaker Patient," Published by Siemens Pacesetter, Inc., 15900 Valley View Court, Sylmar, Calif. 91392 (February 1992).

CONCLUSION

From the above, it is thus seen that the present invention provides a programming tool or aid that facilitates a physician's ability to understand the interaction of an implanted pacemaker with a particular patient so that the physician can better evaluate active clinical problems. The invention also provides a tool assess the performance of the implanted pacemaker over an extended period of time, e.g., on the order of days, weeks, or months. Such is achieved, in part, by providing a summary report of the number of complexes that occur in each of a plurality of pacing states, as well as a distribution of the various rates within each pacing state.

It is also seen from the above description that the invention provides an implantable medical device, such as a pacemaker, that is equipped to track and report its behavior over time and, upon command, provide such information to an attending physician. In particular, it is seen that the invention provides an implantable pacemaker, or other implantable device, that not only detects and records the occurrence of specified events, and in particular pacemaker events or states, but that also determines and records the frequency of occurrence, or the rate, associated with each such detected and recorded event.

It is also seen from the above description that the invention provides a reporting system for use with an implantable pacemaker and an external programmer device that includes dedicated recording circuitry within the implantable pacemaker to record the occurrence and rate of specified pacing events, and processing circuitry in the external programmer programmed to retrieve, process and display the information recorded in the pacemaker in a way that assists a physician in optimally programming the operating parameters of the implantable pacemaker for a particular patient. In particular, it is seen that the pacing data accumulated over a specified time period is displayed in an event/rate histogram and/or an event rate table.

It is noted that several important variations of the invention are also contemplated. For example, the concept of recording the instantaneous rate with each sensed pacing event essentially provides two dimensional data. However, other dimensions could also be added, such as recording amplitude, wave shape, coupling interval, etc., thereby leading to multi-dimensional data.

To illustrate, the event table of the type shown in FIG. 6 may be extended to record the instantaneous sensed amplitude of the intrinsic atrial and ventricular waveforms. In such instance, a number of amplitude bins are defined in the same way that the rate bins are defined. The counter of the bin having the range that includes the measured value is incremented as each event occurs. Presentation of the data on an external programmer is similar to that used for the Event Histogram. Other graph styles, e.g., a line graph, may also be used.

Similarly, through the addition of a few more hardware circuits within the pacemaker, a number of waveform types may be identified, stored, and compared to each subsequent waveform. A count of each type of waveform would thus indicate to the physician which types of waveform were most prevalent. Since the waveform types would be indexed by rate, a correlation between the rate and the waveform type would thus be readily apparent.

Also, the coupling interval between an atrial pulse and its resultant ventricular signal, or the coupling interval between an intrinsic atrial signal and its resultant ventricular signal, is of great interest to the physician in order to evaluate the performance of the heart's AV node. Hence, such coupling interval data may also be recorded. To record this data, a number of coupling interval bins of both types (e.g., PR and PV, respectively) may be defined. Again, the rate at the time of the recording is the index by which a meaningful relationship may be shown on the programmer.

While the invention herein disclosed has been described by means of specific embodiments and applications thereof, numerous modifications and variations could be made thereto by those skilled in the art without departing from the scope of the invention set forth in the claims.

What is claimed is:

1. A method for displaying event counts associated with the operation of an implantable medical device, said implantable medical device including a plurality of event counters that respectively count the occurrence of a plurality of event types associated with the operation of the implantable medical device, sensing and sorting circuits that sense a rate for each event type counted by each of the plurality of event counters, a memory circuit, means for storing and retrieving data from specified memory storage locations within said memory circuit, and a telemetry circuit coupled to the memory circuit for selectively sending event/rate data retrieved from said memory circuit to an external display device, said method comprising the steps of:

(a) counting the occurrence of each of the plurality of specified event types associated with the operation of said implantable medical device in respective ones of said plurality of event counters so that an event count for each event type of said plurality of specified event types is maintained;

(b) determining, using said sensing and sorting circuits, a corresponding rate for each event type of said plurality of specified event types counted in step (a);

(c) storing in said memory circuit said event count and its corresponding rate for each event type of said plurality of specified event types;

(d) selectively retrieving at least a plurality of the event type counts and their corresponding rates stored in said memory element, and sending through said telemetry circuit said retrieved event type counts and their corresponding rates to said external display device; and (e) displaying, and hence reporting, said retrieved event type counts and their corresponding rates with said external display device;

whereby the distribution over time of a plurality of specified event types associated with the operation of the implantable medical device is reported.

2. The method for displaying event type counts, as set forth in claim 1, wherein said external display device comprises a programming device, and wherein steps (d) and (e) include:

establishing a telemetry communication link between said implantable medical device and said programming device, downloading the stored event type counts and corresponding heart rates from the selected plurality of said memory storage locations within said implantable medical device through said established telemetry communication link to said programming device, and displaying said event type counts and corresponding heart rates downloaded to said programming device.

3. The method for displaying event type counts, as set forth in claim 2, wherein the step of displaying said event type counts and corresponding rates comprises generating and displaying an event type rate table, including generating and displaying event types as one of the rows or columns of said event type rate table, and generating and displaying the corresponding rate as the other of the rows or columns thereof, and displaying the event type count associated with a particular event type and rate as a number at the intersection of the row and column corresponding to such particular event type and rate.

4. The method for displaying event type counts, as set forth in claim 2, wherein step (e) comprises determining the relative distribution of the rate in a particular rate range, and generating and displaying an event type/rate histogram as a two dimensional display that includes a plurality of parallel bars for each event type, and making the relative length of each bar so that it corresponds to a rate distribution in the particular rate range.

5. The method for displaying event type counts, as set forth in claim 2, wherein step (e) includes determining the approximate percent of the time over which a particular one of the plurality of specified event types occurred relative to the total time over which all of the specified event types occurred, and generating and displaying an event type histogram as a two dimensional display that includes a plurality of parallel bars for each event type, and making the relative length of each of said parallel bars within said event type histogram represent the approximate percent of the time over which said particular one of the plurality of specified event types occurred relative to the total time over which all of the specified event types occurred.

6. The method for displaying event type counts, as set forth in claim 2, wherein step (e) includes determining the approximate percent that a particular one of the event types occurred relative to the total number of times that all of the event types occurred, and generating and displaying an event type histogram as a two dimensional display that includes a plurality of parallel bars for each event type, and making the relative length of each of said parallel bars within said event type histogram represent the approximate percent that the particular one of the event types occurred relative to the total number of times that all of the event types occurred.

7. The method for displaying event type counts, as set forth in claim 2, wherein said programming device includes a processor for computing selected statistical information based on the downloaded event counts maintained in said event counters and the corresponding rates determined for each event type, and wherein said method further includes:

computing selected statistical information associated with the downloaded event type counts and rates, and displaying the selected statistical information thus computed.

8. The method for displaying event type counts, as set forth in claim 7, further including computing the selected statistical information associated with the downloaded event type counts and rates to include an indication of the percent of the total time during which event types were counted corresponding to the occurrence of a particular counted event type.

9. The method for displaying event type counts, as set forth in claim 7, further including computing the selected statistical information associated with the downloaded event type counts and rates to include an indication of the percent of all the total counted event types corresponding to the occurrence of a particular counted event type.

10. The method for displaying event type counts, as set forth in claim 2, further including defining a specified sample interval and sampling the event types that occur within said implantable medical device at the conclusion of the specified sample interval, whereby the counting of a particular event type and the determining of the corresponding rate of such counted particular event type occurs only at the conclusion of said specified sample interval.

11. The method for displaying event type counts, as set forth in claim 10, wherein the step of defining a selected sample interval includes defining a plurality of possible sample intervals, said plurality of possible sample intervals including a sample interval defined by: (1) the occurrence of each event type, (2) the conclusion of every T1 seconds, or (3) the conclusion of every T2 seconds, where T1 is a time interval greater than the longest interval between counted event types, and T2 is a time interval greater than T1; and then selecting one of said possible sample intervals as the specified sample interval.

12. The method for displaying event type counts, as set forth in claim 2, wherein said implantable medical device comprises an implantable pacemaker having means for sensing a natural cardiac contraction and means for generating a stimulation pulse, and wherein the step of counting specified event types includes counting sensed event types and counting paced event types, a sensed event type including the sensing of a natural contraction, and a paced event type including the generating of a stimulation pulse.

13. The method for displaying event type counts, as set forth in claim 12, wherein said implantable pacemaker comprises a dual-chamber pacemaker, and wherein said means for sensing a natural cardiac contraction includes means for sensing a P-wave and means for sensing an R-wave, a P-wave representing the natural contraction of the atrium and an R-wave representing the natural contraction of the ventricle, and further wherein said means for generating a stimulation pulse includes means for issuing an A-pulse and means for issuing a V-pulse, an A-pulse comprising a stimulation pulse delivered to the atrium, and a V-pulse comprising a stimulation pulse delivered to the ventricle; and wherein the step of counting specified event types includes counting:
- a sensed P-wave followed by a sensed V-pulse (a "PV" event type);
- a sensed P-wave followed by a sensed R-wave (a "PR" event type);
- an issued A-pulse followed by an issued V-pulse (an "AV" event type); and
- either a sensed R-wave or an issued V-pulse followed by a sensed R-wave, which sequence of ventricular events without an appropriate intervening atrial event comprises a premature ventricular event (a "PVE").

14. The method for displaying event type counts, as set forth in claim 13, wherein said dual-chamber pacemaker has a maximum tracking rate (MTR) associated with its operation, and means for determining if the corresponding rate for each event type is at least as great as said maximum tracking rate, and wherein the step of counting specified event types further includes counting:
- a sensed P-wave at the maximum tracking rate followed by an issued V-pulse (a "P@MTR-V" event type); and
- a sensed P-wave at the maximum tracking rate followed by a sensed R-wave (a "P@MTR-R" event type).

15. The method for displaying event type counts, as set forth in claim 2, wherein said programming device includes means for issuing selected commands, including a clear command, and transmitting said selected commands to said implantable medical device through said telemetry communication link, and wherein said method further includes the step of selectively clearing the stored event type counts held in said event counters and corresponding rates maintained within said implantable medical device by issuing a clear command from said programming device.

16. The method for displaying event type counts, as st forth in claim 15, wherein the selected commands that may be issued by said programming device include commands for altering an operating mode of said implantable medical device, and wherein said programming device includes means for automatically generating and issuing said clear command whenever the operating mode of said implantable medical device is altered by said programming means.

17. The method for displaying event type counts, as set forth in claim 2, wherein step (c) of storing the event type counts and rates in said memory element includes selecting a plurality of memory storage locations whereat a particular one of said plurality of specified event types may be stored, with each one of said plurality of memory storage locations being associated with a different range of rates for particular specified event types, and storing event type counts for a first type that occur at a rate falling within a first range in a first memory storage location, storing event type counts of the first type that occur at a rate falling within a second range in a second memory storage location, storing event type counts of a second type that occur at a rate falling within the first range in a third memory storage location, and so on, with the count of a particular event type that occurred within a particular range of rates being stored in a separate memory storage location.

18. The method for displaying event type counts, as set forth in claim 1, wherein step (b) of determining a corresponding rate comprises: determining which of a plurality of ranges of rate corresponds to each event type of said plurality of specified events covered in step (a).

19. The method for displaying event type counts, as set forth in claim 1, wherein step (b) of determining a corresponding rate comprises: determining a corresponding ventricular heart rate for each event type of said plurality of specified events counted in step (a).

20. The method for displaying event type counts, as set forth in claim 1, wherein step (b) of determining a corresponding rate comprises: determining a corresponding atrial heart rate for each event type of said plurality of specified events counted in step (a).

21. The method for displaying event type counts as set forth in claim 1, wherein step (b) of determining a corresponding rate comprises:
- determining a native heart rate and a paced heart rate, and selecting one of said native heart rate and paced heart rate as the corresponding rate for each event type.

22. A method for recording and reporting the distribution of pacing event types associated with the operation of an implantable pacemaker, said implantable pacemaker including a plurality of event counters that respectively count the occurrence of a plurality of event types associated with the operation of the implantable pacemaker, sensing and sorting circuits that sense a rate for each event type counted by each of the plurality of event counters, a memory circuit, means for storing and retrieving data from specified memory storage locations within said memory circuit, and a telemetry circuit coupled to the memory circuit for selectively telemetering data retrieved from said memory circuit, said method comprising:
(a) counting the number of occurrences of a plurality of pacing event types associated with the operation of the implantable pacemaker in respective ones of said plurality of event counters so that an event count for each event type of said plurality of specified event types is maintained;

(b) determining using said sensing and sorting circuits the rate of occurrence of each event type counted in step (a);

(c) storing in said memory circuit the count of each of said plurality of pacing event types made in step (a) as a function of the rate at which said pacing event type occurs as determined in step (b);

(d) establishing a telemetry communication link with said telemetry circuit with an external device;

(e) retrieving selected ones of the stored counts and corresponding rate from said memory circuit; and (f) reporting the stored counts for each of the plurality of pacing event types that occurred at a specified rate to said external device through said established telemetry communication link.

23. The method, as set forth in claim 22, wherein step (b) comprises classifying the rate at which the counted pacing event types occurred as belonging to one of a plurality of rate ranges, and wherein step (c) includes storing the count of each of said plurality of pacing event types as a function of one of said plurality of rate ranges.

24. The method, as set forth in claim 23, wherein step (f) comprises reporting the stored counts for each of the plurality of pacing event types as belonging to one of said rate ranges.

25. The method, as set forth in claim 24, wherein said external device includes means for receiving, processing and displaying data received through the telemetry communication link, and wherein step (f) includes processing and then selectively displaying the stored counts for each of the plurality of pacing event types in a graphical format that identifies a relative rate at which each displayed stored count occurred.

26. The method, as set forth in claim 25, wherein said implantable pacemaker includes means for sensing a natural cardiac contraction and means for generating a stimulation pulse, and wherein the step of counting the number of occurrences of a plurality of pacing event types includes counting sensed events and counting paced events, a sensed event including the sensing of a natural contraction, and a paced event including the generating of a stimulation pulse.

27. The method, as set forth in claim 26, wherein said implantable pacemaker comprises a dual-chamber pacemaker, and wherein said means for sensing a natural cardiac contraction includes means for sensing a P-wave and means for sensing an R-wave, a P-wave representing the natural contraction of the atrium and an R-wave representing the natural contraction of the ventricle, and further wherein said means for generating a stimulation pulse includes means for issuing an A-pulse and means for issuing a V-pulse, an A-pulse comprising a stimulation pulse delivered to the atrium, and a V-pulse comprising a stimulation pulse delivered to the ventricle; and wherein the step of counting the number of occurrences of a plurality of pacing event types includes counting:

a sensed P-wave followed by a sensed V-pulse (a "PV" event type);

a sensed P-wave followed by a sensed R-wave (a "PR" event type);

an issued A-pulse followed by an issued V-pulse (an "AV" event type); and an issued A-pulse followed by a sensed R-wave (an "AR" event type).

28. The method, as set forth in claim 27, wherein said dual-chamber pacemaker has a maximum tracking rate (MTR) associated with its operation, and means for determining if the corresponding ate for each event type is at least as great as said maximum tracking rate, and wherein the step of counting the number of occurrences of a plurality of pacing event types further includes counting:

either a sensed R-wave or an issued V-pulse followed by a sensed R-wave, which sequence of ventricular events without an appropriate intervening atrial event comprises a premature ventricular event (a "PVE").

a sensed P-wave at the maximum tracking rate followed by an issued V-pulse (a "P@MTR-V" event type); and a sensed P-wave at the maximum tracking rate followed by a sensed R-wave (a "P@MTR-V" event type).

29. The method, as set forth in claim 28, further including determining the approximate percent of the time over which a particular one of the plurality of specified pacing event types occurred relative to the total time over which all of the specified pacing event types occurred, and displaying as part of said graphical format an event type histogram, said event type histogram being displayed as a two dimensional display of a plurality of parallel bars, each bar corresponding to a particular one of said plurality of specified pacing event types, and making the relative length of each of said parallel bars within said event type histogram represent the approximate percent of the time over which said particular one of the plurality of specified pacing event types occurred relative to the total time over which all of the specified pacing events occurred.

30. The method, as set forth in claim 25, further including determining the relative distribution of the rate in a particular rate range, and displaying as part of said graphical format an event type histogram, said event type histogram being displayed as a two dimensional display of a plurality of parallel bars, each bar corresponding to a particular one of said plurality of specified pacing event types, and making the relative length of each bar in the display correspond to the rate of said particular one of said plurality of specified pacing event types.

31. The method, as set forth in claim 25, further including displaying as part of said graphical format an event type rate table, including generating and displaying pacing event types as one of the rows or columns of said event type rate table, and generating and displaying the rate ranges as the other of the rows or columns thereof, and displaying the pacing event type count associated with a particular pacing event type and a particular range of rates as a number at the intersection of the row and column corresponding to such particular event type and rate range.

32. The method, as set forth in claim 25, further including computing statistical information with the processing means of said external device from the pacing event type counts and the corresponding rate ranges telemetered from said implantable pacemaker, and displaying as part of said graphical format said selected statistical information.

33. A method of reporting the number of pacing events of a prescribed plurality of pacing event types that occur during the operation of an implantable pacemaker in combination with the relative frequency of occurrence of such pacing event types, said implantable pacemaker including sensing means for sensing and counting the occurrence of each of said plurality of pacing event types within one of a plurality of rate ranges, a memory in which a count of each of said plurality of pacing event types that occurs within one of the plurality of rate ranges is maintained, and telemetry means for downloading the contents of the memory to an external programming device, said external programming device having processing means for processing the downloaded contents of the memory in a prescribed manner, and display means for displaying selected graphical representations of the downloaded contents of the memory, said method comprising the steps of:

(a) retrieving the counts from said memory of each of said plurality of pacing event types that occurred within each of said plurality of rate ranges;

(b) downloading the retrieved counts for each of said plurality of rate ranges to the external programming device;

(c) determining from the counts retrieved in step (a) and downloaded in step (b) an approximate distribution of the pacing event types over time; and (d) simultaneously displaying the distribution of the pacing event types over time determined in step (c) for each of said plurality of pacing event types.

34. The method, as set forth in claim 33, wherein step (c) comprises:

creating an event type/rate table having rows and columns, including designating said plurality of pacing event types as one of the rows or columns of said event type/rate table, and designating the rate ranges as the other of the rows or columns thereof, and placing the event type count associated with a particular one of said plurality of pacing event types and its corresponding rate range as a number at the intersection of the row and column corresponding to such particular one of said plurality of pacing event types and its corresponding rate range, and computing a total of the event type counts for each of said plurality of pacing event types so as to provide a total event type count, regardless of rate range, for each of said plurality of pacing event types, and computing an estimate of the total time over which the pacing event types have occurred from said total event type count, and determining said approximate distribution of a given one of said pacing event types over time as a function of said total event type count and said estimate of the total time.

35. The method, as set forth in claim 34, wherein step (d) includes displaying said event type/rate table.

36. The method, as set forth in claim 34, wherein step (d) includes creating, using said processing means of said external programming device, a stacked histogram as a two dimensional graphical display, displaying said stacked histogram, using the display means of said external programming device, so that said prescribed plurality of pacing event types are identified along a first axis, and an event type count is identified along a second axis, depicting the total number of event type counts associated with a particular one of said plurality of pacing event types as a bar extending out from said first axis at a location on said first axis corresponding to said particular one of said pacing event types, said bar paralleling said second axis, making the length of said bar equal to the total number of event type counts for said particular one of said pacing event types as determined from said second axis, and segmenting said bar as a function of said plurality of rate ranges so that the number of occurrences of said particular one of said pacing event types that occurred within a give rate range is proportional to the length of an identifiable segment of said bar relative to total length of said bar.

37. The method, as set forth in claim 34, wherein steps (c) and (d) include determining the approximate total time during which each of the plurality of pacing event types occurred relative to the approximate total time over which all of said of said plurality of pacing event types occurred, and generating and displaying an event type histogram made up of a plurality of parallel bars by designating each bar to correspond to one of said plurality of pacing event types, and by making the relative length of a given bar to provide a graphical representation of the approximate total time during which said one of the plurality of pacing event types occurred relative to the approximate total time over which all of said plurality of pacing event types occurred.

38. The method, as set forth in claim 37, further including displaying a number at one end of each of said plurality of parallel bars that indicates the percent of the approximate total time that the corresponding pacing event type occurred.

39. A system for reporting the number and relative frequency of pacing event types of a prescribed plurality of pacing event types that occur during the operation of an implantable pacemaker comprising:

counting means within said pacemaker for counting and storing the number of occurrences of each of said plurality of pacing event types that occurs within a prescribed rate range, said counting means including:

event type determining means for determining the occurrence of each of said plurality of pacing event types, rate determining means for determining the frequency of occurrence of each of said plurality of pacing event types, and a memory wherein a count of the number of occurrences of each of said plurality of pacing event types is maintained, as well as an indication of the relative frequency of occurrence of each of said plurality of pacing event types;

downloading means for selectively downloading event/rate data from said pacemaker to an external programming device, said event/rate data including the number of occurrences counted and stored in said counting means and their corresponding frequency of occurrence;

determining means within said programming device for determining from said event/rate data an approximate distribution of the pacing event types over time; and display means for selectively displaying the distribution of the pacing event types over time determined by said determining means for each of said plurality of pacing event types.

40. The reporting system, as set forth in claim 39, wherein said determining means comprises data processing means, said data processing means including:

means for creating an event type rate table from said event/rate data received from said pacemaker through said downloading means, said event type rate table having said plurality of pacing event types as one of the rows or columns thereof, and having a plurality of rate ranges as the other of the rows or columns thereof, and means for computing and placing the event type count associated with a particular one of said plurality of pacing event types and its corresponding rate range as a number at the intersection of the row and column corresponding to such particular one of said plurality of pacing event types and its corresponding rate range, means for totaling the event counts for each of said plurality of pacing event types so as to provide a total event count, regardless of rate range, for each of said plurality of pacing event types, and means for estimating the total time over which the pacing event types have occurred based on said total event count, said approximate distribution of said pacing event types over time being a function of said total event count and approximate total time.

41. The reporting system, as set forth in claim 40, wherein said data processing means includes means for generating a graphical image that is displayed by said display means, said graphical image including a two-dimensional event type histogram that depicts a plurality of parallel bars, each bar corresponding to one of said plurality of pacing event types, the relative length of a given bar being set by said data processing means to provide a graphical representation of the approximate total time during which said one of the plurality of pacing event types occurred relative to the approximate total time over which all of said plurality of pacing event types occurred.

42. The reporting system, as set forth in claim 41, wherein said display means comprises an integral part of said programming device.

43. The reporting system, as set forth in claim 42, wherein the graphical image generated by said data processing means and displayed by said display means includes a number at one end of each of said plurality of parallel bars, said number being computed by said processing means, that indicates the percent of the approximate total time that the corresponding pacing event type occurred.

44. The reporting system, as set forth in claim 40, wherein said memory includes a plurality of addressable memory locations, and means for selectively addressing a selected one of said plurality of memory locations for the purpose of storing data therein or reading data therefrom, a plurality of groups of memory locations being assigned to respective pacing event types, with each memory storage location within each group being assigned to a prescribed rate range, the number of occurrences of a given pacing event type that occur within a particular rate range being stored in the memory location assigned to said particular rate range for the group of memory locations corresponding to said given pacing event type.

45. The reporting system, as set forth in claim 44, wherein said implantable pacemaker includes sensing means for sensing a natural cardiac contraction and stimulation means for generating a stimulation pulse, and wherein the prescribed plurality of pacing event types that are reported by said reporting system includes: (1) a natural cardiac contraction sensed by said sensing means; and (2) a stimulation pulse generated by said stimulation means.

46. The reporting system as set forth in claim 44, wherein said implantable pacemaker comprises a dual-chamber pacemaker having means for sensing a P-wave and an R-wave, a P-wave representing the natural contraction of the atrium and an R-wave representing the natural contraction of the ventricle, and means for issuing an A-pulse and a V-pulse, an A-pulse being a stimulation pulse delivered to the atrium, and a V-pulse being a stimulation pulse delivered to the ventricle; and wherein the prescribed plurality of pacing event types that are reported by said reporting system includes:

a P-wave followed by a V-pulse (a "PV" event type);

a P-wave followed by an R-wave (a "PR" event type);

an A-pulse followed by a V-pulse (an "AV" event type); and an A-pulse followed by an R-wave (an "AR" event type).

47. The reporting system, as set forth in claim 46, wherein said dual-chamber pacemaker has a maximum tracking rate (MTR) associated with its operation, and wherein the prescribed plurality of pacing event types that are reported by said reporting system further includes:

either a sensed R-wave or an issued V-pulse followed by a sensed R-wave, which sequence of ventricular events without an appropriate intervening atrial event comprises a premature ventricular event (a "PVE").

a P-wave at the maximum tracking rate followed by a V-pulse (a "P@MTR-V" event type); and a P-wave at the maximum tracking rate followed by an R-wave (a "P@MTR-R" event type).

48. A reporting system comprising:

an implantable pacemaker, said implantable pacemaker having means for detecting and reporting the occurrence and relative rate of occurrence of a plurality of pacing event types associated with the operation of said implantable pacemaker, said detected and reported occurrences and rates comprising event/rate data;

a programming device for use with said implantable pacemaker, said programming device including communication means for transferring control data to and receiving event/rate data from said implantable pacemaker; and processing means within said programming device for processing said event/rate data and creating and displaying a graphical display that indicates the number and relative rate of occurrence of each of the plurality of pacing event types detected and reported by said implantable pacemaker.

49. The reporting system, as set forth in claim 48, wherein said processing means includes:

means for determining a total event count for each of said plurality of pacing event types, regardless the relative rate of occurrence for each of said plurality of pacing event types; and means for estimating the total time over which the pacing event types have occurred from said total event count.

50. The reporting system, as set forth in claim 49, wherein said graphical display comprises an event type histogram that shows a plurality of parallel bars, each bar of said plurality of parallel bars having one of said plurality of pacing event types assigned thereto, and wherein said processing means sets the length of each bar to represent the relative rate of occurrence of the pacing event type assigned to each bar.

51. The reporting system, as set forth in claim 50, wherein the processing means determines the approximate total time during which each pacing event type occurred and the approximate total time over which all of the plurality of pacing event types occurred, and sets the length of each bar of said plurality of parallel bars of said event type histogram to graphically represent the approximate total time during which the pacing event type assigned to such bar occurred relative to the approximate total time over which all of said plurality of pacing event types occurred.

52. The reporting system, as set forth in claim 49, wherein said processing means includes within the graphical display an event type/heart rate table, said event type/heart rate table having rows and columns, with said plurality of pacing event types being designated as one of the rows or columns thereof, and with a plurality of rate ranges being designated as the other of the rows or columns thereof, and further with an event count associated with a particular one of said plurality of pacing event types and its corresponding rate range being placed as a number at the intersection of the row and column corresponding to such particular one of said plurality of pacing event types and its corresponding rate range.

53. The reporting system, as set forth in claim 48, wherein said implantable pacemaker includes sensing circuits for sensing natural cardiac events and pacing circuits for generating paced events, and wherein said prescribed plurality of pacing event types detected and reported by said implantable pacemaker includes a natural event sensed by the sensing circuits within said implantable pacemaker, and a paced event created by the pacing circuits within said implantable pacemaker.

54. The reporting system, as set forth in claim 43, wherein said implantable pacemaker comprises a dual chamber pacemaker, and wherein said sensing circuits include means for sensing P-waves and R-waves, and wherein said pacing circuits include means for issuing V-pulses and A-pulses, and wherein said prescribed plurality of pacing event types includes:
- a sensed P-wave followed by an issued V-pulse (a "PV" event type);
- a sensed P-wave followed by a sensed R-wave (a "PR" event type);
- an issued A-pulse followed by an issued V-pulse (an "AV" event type); and
- an issued A-pulse followed by a sensed R-wave (an "AR" event type);
- a premature ventricular event (a "PVE");
- wherein said P-wave represents the sensed natural contraction of the atrium of a heart coupled to said implantable pacemaker, said R-wave represents the sensed natural contraction of the ventricle of the heart, said A-pulse is a stimulation pulse generated by said implantable pacemaker for delivery to the atrium, said V-pulse is a stimulation pulse generated by said implantable pacemaker for delivery to the ventricle, and wherein said PVE is an R-wave that immediately follows a prior ventricular event, which ventricular event is either a V-pulse or an R-wave, without an intervening atrial event, which atrial event is either an A-pulse or a P-wave.

55. The reporting system, as set forth in claim 54, wherein said implantable pacemaker has a maximum tracking rate (MTR) associated with its operation, and wherein said prescribed plurality of pacing event types further includes:
- a sensed P-wave at the maximum tracking rate followed by an issued V-pulse (a "P@MTR-V" event type); and
- a sensed P-wave at the maximum tracking rate followed by a sensed R-wave (a "P@MTR-R" event type).

* * * * *

UNITED STATES PATENT AND TRADEMARK OFFICE
CERTIFICATE OF CORRECTION

PATENT NO. : 5,309,919

DATED : May 10, 1994

INVENTOR(S) : Jeffery D. Snell, et al.

It is certified that error appears in the above-indentified patent and that said Letters Patent is hereby corrected as shown below:

In col. 16, line 33, delete "No. X 8)" and substitute therefor —No. X 8))—.

In Claim 1, col. 29, line 22, delete "memory element" and substitute therefor —memory circuit—.

In Claim 13, col. 31, line 31, delete "a sensed V-pulse" and substitute therefor —an issued V-pulse—.

In Claim 13, col. 31, line 36, delete "and".

In Claim 13, col. 31, after line 36, insert the following paragraph: —an issued A-pulse followed by a sensed R-wave (an "AR" event type); and—.

In Claim 16, col. 31, line 67, delete "st" and substitute therefor —set—.

In Claim 17, col. 32, line 10, delete "memory element" and substitute therefor —memory circuit—.

In Claim 17, col. 32, line 16, delete "for" and substitute therefor —of—.

In Claim 27, col. 33, line 59, delete "a sensed V-pulse" and substitute therefor —an issued V-pulse—.

In Claim 28, col. 34, line 11, delete ")." and substitute therefor —);—.

In Claim 28, col. 34, line 16, delete "MTR-V" and substitute therefor —MTR-R—.

UNITED STATES PATENT AND TRADEMARK OFFICE
CERTIFICATE OF CORRECTION

PATENT NO. : 5,309,919

DATED : May 10, 1994

INVENTOR(S) : Jeffery D. Snell, et al.

It is certified that error appears in the above-indentified patent and that said Letters Patent is hereby corrected as shown below:

In Claim 47, col. 38, line 35, delete ")." and substitute therefor —);—.

In Claim 49, col. 38, line 62, after "regardless" insert —of—.

In Claim 52, col. 39, line 23, delete "type/heart rate" and substitute therefor —type/rate—.

In Claim 52, col. 39, line 24, delete "type/heart rate" and substitute therefor —type/rate—.

Signed and Sealed this

Eighteenth Day of February, 1997

Attest:

BRUCE LEHMAN

Attesting Officer

Commissioner of Patents and Trademarks